US012655410B2

(12) United States Patent
Michels et al.

(10) Patent No.: US 12,655,410 B2
(45) Date of Patent: Jun. 16, 2026

(54) STABLE PROTEASE VARIANTS

(71) Applicant: EW NUTRITION GMBH, Visbek (DE)

(72) Inventors: Andreas Michels, Düsseldorf (DE); Andreas Scheidig, Westoverledigen (DE); Christian Elend, Cologne (DE); Claudia Krapp, Cologne (DE); Thomas Horn, Aachen (DE)

(73) Assignee: EW NUTRITION GMBH, Visbek (DE)

(*) Notice: Subject to any disclaimer, the term of this patent is extended or adjusted under 35 U.S.C. 154(b) by 1025 days.

(21) Appl. No.: 17/850,103

(22) Filed: Jun. 27, 2022

(65) Prior Publication Data

US 2023/0092791 A1 Mar. 23, 2023

Related U.S. Application Data

(63) Continuation-in-part of application No. 16/471,507, filed as application No. PCT/EP2017/084452 on Dec. 22, 2017, now Pat. No. 11,396,648.

(30) Foreign Application Priority Data

Dec. 22, 2016 (EP) .................................... 16206367

(51) Int. Cl.
*C12N 9/54* (2006.01)
*A23K 20/189* (2016.01)
*C11D 3/386* (2006.01)

(52) U.S. Cl.
CPC .............. *C12N 9/54* (2013.01); *A23K 20/189* (2016.05); *C11D 3/386* (2013.01); *C12Y 304/21* (2013.01)

(58) Field of Classification Search
CPC ........ C12N 9/54; A23K 20/189; C11D 3/386; C12Y 304/21
See application file for complete search history.

(56) References Cited

U.S. PATENT DOCUMENTS

2005/0265932 A1 12/2005 Kappler et al.

FOREIGN PATENT DOCUMENTS

| | | | |
|---|---|---|---|
| CN | 105555300 | A | 8/2014 |
| WO | WO2013/023151 | | 2/2013 |
| WO | WO2015023728 | A | 2/2015 |
| WO | WO2016/200880 | | 12/2016 |

OTHER PUBLICATIONS

International Search Report and Written Opinion mailed on Jan. 28, 2020 for Application No. PCT/US19/058156, which was filed on Oct. 25, 2019 (Applicant: US Government as Represented by the Dept of Veterans Affairs) (16 pages).

Office Action mailed Oct. 10, 2022 for CN Application No. 201780087051.4, which was filed on Dec. 22, 2017 (Applicant: EW Nutrition GMBH).

Wolf et al. "Engineering of Kuma030: A Gliadin Peptidase that Rapidly Degrades Immunogenic Gliadin Peptides in Gastric Conditions" Journal of the American Chemical Society, vol. 137, No. 40, Oct. 14, 2015, pp. 13106-13113.

Office Action mailed on May 24, 2022 by the Korean Patent Office for Patent Application No. 10-2019-7020123, which was filed on Jul. 11, 2019 (Inventor—Michels et al.; Applicant—EW Nutrition GmbH.) (4 pages).

International Preliminary Report on Patentability was mailed on Jun. 25, 2019 by the International Searching Authority for International Application No. PCT/EP2017/084452, filed on Dec. 22, 2017 and published as WO 2018/115473 on Jun. 28, 2018.

European Search Report and Written Opinion mailed on Aug. 31, 2017 by the EPO for EP Application No. 16206367 (Applicant EW Nutrition GMBH) (17 pages).

Okubo et al. 2006 "Processing, catalytic activity and crystal structures fo kumamolisin—As with an engineered active site", FEBS J (2006); 273(11):2563-76.

Cadwell et al., "Mutagenic PCR", PCR Methods Appl. (1994); 3(6):S136-40.

Hsieh; et al., "Protein engineering: single or multiple site-directed mutagenesis", Methods Mol. Biol.(2013); 978:173-86.

Packer, et al., "Methods for the directed evolution of proteins", Nat Rev Genet. (2015);16(7):379-94.

Oda,K et al., " Pepstatin-Insensitive Carboxyl Proteinases from Prokaryotes", Adv Exp Med Biol. (1998);436:349-53.

Terashita, T. et al., "*Streptomyces* pepsin Inhibitor-Insensitive Carboxyl Proteinase from Lentinus edodes+", Agric Chem, (1981), 45:1937-1943.

Wlodawer Al, et al., "Structural and enzymatic properties of the sedolisin family of serine-carboxyl peptidases", Biochim Pol. (2003);50(1):81-102.

Tsuruoka, N., et al., "Collagenolytic Serine-Carboxyl Proteinase from Alicyclobacillus sendaiensis Strain NTAP-1 Purification, Characterization, Gene Cloning, and Heterologous Expression", Applied and Environmental Microbiology, vol. 69, No. 1, pp. 162-169, XP055042507 [A] 1-15 * figure 3 * , Jan. 1, 2003.

Wolf, C. et al., "Engineering of Kuma030: A Gliadin Peptidase That Rapidly Degrades Immunogenic Gliadin in Gastric Conditions", J Am Chem Soc. (2015);137(40):13106-13.

Wolf, C. et al "Engineering of Kuma030: a gliadin peptidase that rapidly degrades immunogenic gladin peptides in gastric conditions", Journal of the American Chemical Society, (2015), pp. sI-s9, tables 1,2.

*Primary Examiner* — Iqbal H Chowdhury
(74) *Attorney, Agent, or Firm* — BALLARD SPAHR LLP

(57) ABSTRACT

The present invention relates to a protease variant which is at least 90% identical to the full length amino acid sequence of a Kumamolisin AS backbone as set forth in any of SEQ ID NOs 1-3, while maintaining proteolytic activity, or a fragment, fraction or shuffled variant thereof maintaining proteolytic activity, which protease variant demonstrates altered or improved stability compared to the Kumamolisin AS wildtype as set forth in SEQ ID NO 4, or the Kumamolisin AS backbone as set forth in any of SEQ ID NOs 1-3.

13 Claims, 5 Drawing Sheets

Specification includes a Sequence Listing.

SEQUENCE LISTING

<160> NUMBER OF SEQ ID NOS: 5

<210> SEQ ID NO 1
<211> LENGTH: 552
<212> TYPE: PRT
<213> ORGANISM: artificial
<220> FEATURE:
<223> OTHER INFORMATION: Kumamolisin 1 proenzyme, backbone variant
(N-terminal M is lacking)

<400> SEQUENCE: 1

Ser Asp Met Glu Lys Pro Trp Lys Glu Gly Glu Glu Ala Arg Ala Val
1 5 10 15

Leu Gln Gly His Ala Arg Ala Gln Ala Pro Gln Ala Val Asp Lys Gly
20 25 30

Pro Val Ala Gly Asp Glu Arg Met Ala Val Thr Val Val Leu Arg Arg
35 40 45

Gln Arg Ala Gly Glu Leu Ala Ala His Val Glu Arg Gln Ala Ala Ile

-continued

```
    50                  55                  60

Ala Pro His Ala Arg Glu His Leu Lys Arg Glu Ala Phe Ala Ala Ser
65                  70                  75                  80

His Gly Ala Ser Leu Asp Asp Phe Ala Glu Leu Arg Arg Phe Ala Asp
                85                  90                  95

Ala His Gly Leu Ala Leu Asp Arg Ala Asn Val Ala Ala Gly Thr Ala
            100                 105                 110

Val Leu Ser Gly Pro Val Asp Ala Ile Asn Arg Ala Phe Gly Val Glu
        115                 120                 125

Leu Arg His Phe Asp His Pro Asp Gly Ser Tyr Arg Ser Tyr Leu Gly
    130                 135                 140

Glu Val Thr Val Pro Ala Ser Ile Ala Pro Met Ile Glu Ala Val Leu
145                 150                 155                 160

Gly Leu Asp Thr Arg Pro Val Ala Arg Pro His Phe Arg Met Gln Arg
                165                 170                 175

Arg Ala Glu Gly Gly Phe Glu Ala Arg Ser Gln Ala Ala Ala Pro Thr
            180                 185                 190

Ala Tyr Thr Pro Leu Asp Val Ala Gln Ala Tyr Gln Phe Pro Glu Gly
        195                 200                 205

Leu Asp Gly Gln Gly Gln Cys Ile Ala Ile Ile Glu Leu Gly Gly Gly
    210                 215                 220

Tyr Asp Glu Ala Ser Leu Ala Gln Tyr Phe Ala Ser Leu Gly Val Pro
225                 230                 235                 240

Ala Pro Gln Val Val Ser Val Ser Val Asp Gly Ala Ser Asn Gln Pro
                245                 250                 255

Thr Gly Asp Pro Ser Gly Pro Asp Gly Glu Val Glu Leu Asp Ile Glu
            260                 265                 270

Val Ala Gly Ala Leu Ala Pro Gly Ala Lys Phe Ala Val Tyr Phe Ala
        275                 280                 285

Pro Asn Thr Asp Ala Gly Phe Leu Asp Ala Ile Thr Thr Ala Ile His
    290                 295                 300

Asp Pro Thr Leu Lys Pro Ser Val Val Ser Ile Ser Trp Gly Gly Pro
305                 310                 315                 320

Glu Asp Ser Trp Thr Ser Ala Ala Ile Ala Ala Met Asn Arg Ala Phe
                325                 330                 335

Leu Asp Ala Ala Ala Leu Gly Val Thr Val Leu Ala Ala Ala Gly Asp
            340                 345                 350

Ser Gly Ser Thr Asp Gly Glu Gln Asp Gly Leu Tyr His Val Asp Phe
        355                 360                 365

Pro Ala Ala Ser Pro Tyr Val Leu Ala Cys Gly Gly Thr Arg Leu Val
    370                 375                 380

Ala Ser Gly Gly Arg Ile Ala Gln Glu Thr Val Trp Asn Asp Gly Pro
385                 390                 395                 400

Asp Gly Gly Ala Thr Gly Gly Gly Val Ser Arg Ile Phe Pro Leu Pro
                405                 410                 415

Ala Trp Gln Glu His Ala Asn Val Pro Pro Ser Ala Asn Pro Gly Ala
            420                 425                 430

Ser Ser Gly Arg Gly Val Pro Asp Leu Ala Gly Asn Ala Asp Pro Ala
        435                 440                 445

Thr Gly Tyr Glu Val Val Ile Asp Gly Glu Ala Thr Val Ile Gly Gly
    450                 455                 460

Thr Ser Ala Val Ala Pro Leu Phe Ala Ala Leu Val Ala Arg Ile Asn
465                 470                 475                 480
```

```
Gln Lys Leu Gly Lys Ala Val Gly Tyr Leu Asn Pro Thr Leu Tyr Gln
                485                 490                 495

Leu Pro Ala Asp Val Phe His Asp Ile Thr Glu Gly Asn Asn Asp Ile
            500                 505                 510

Ala Asn Arg Ala Gln Ile Tyr Gln Ala Gly Pro Gly Trp Asp Pro Cys
        515                 520                 525

Thr Gly Leu Gly Ser Pro Ile Gly Val Arg Leu Leu Gln Ala Leu Leu
    530                 535                 540

Pro Ser Ala Ser Gln Pro Gln Pro
545                 550


<210> SEQ ID NO 2
<211> LENGTH: 587
<212> TYPE: PRT
<213> ORGANISM: artificial
<220> FEATURE:
<223> OTHER INFORMATION: Kumamolisin 1 proenzyme backbone variant with
      leader sequence and His tag

<400> SEQUENCE: 2

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Ser Asp Met
            20                  25                  30

Glu Lys Pro Trp Lys Glu Gly Glu Glu Ala Arg Ala Val Leu Gln Gly
        35                  40                  45

His Ala Arg Ala Gln Ala Pro Gln Ala Val Asp Lys Gly Pro Val Ala
    50                  55                  60

Gly Asp Glu Arg Met Ala Val Thr Val Val Leu Arg Arg Gln Arg Ala
65                  70                  75                  80

Gly Glu Leu Ala Ala His Val Glu Arg Gln Ala Ala Ile Ala Pro His
                85                  90                  95

Ala Arg Glu His Leu Lys Arg Glu Ala Phe Ala Ala Ser His Gly Ala
            100                 105                 110

Ser Leu Asp Asp Phe Ala Glu Leu Arg Arg Phe Ala Asp Ala His Gly
        115                 120                 125

Leu Ala Leu Asp Arg Ala Asn Val Ala Ala Gly Thr Ala Val Leu Ser
    130                 135                 140

Gly Pro Val Asp Ala Ile Asn Arg Ala Phe Gly Val Glu Leu Arg His
145                 150                 155                 160

Phe Asp His Pro Asp Gly Ser Tyr Arg Ser Tyr Leu Gly Glu Val Thr
                165                 170                 175

Val Pro Ala Ser Ile Ala Pro Met Ile Glu Ala Val Leu Gly Leu Asp
            180                 185                 190

Thr Arg Pro Val Ala Arg Pro His Phe Arg Met Gln Arg Arg Ala Glu
        195                 200                 205

Gly Gly Phe Glu Ala Arg Ser Gln Ala Ala Ala Pro Thr Ala Tyr Thr
    210                 215                 220

Pro Leu Asp Val Ala Gln Ala Tyr Gln Phe Pro Glu Gly Leu Asp Gly
225                 230                 235                 240

Gln Gly Gln Cys Ile Ala Ile Ile Glu Leu Gly Gly Gly Tyr Asp Glu
                245                 250                 255

Ala Ser Leu Ala Gln Tyr Phe Ala Ser Leu Gly Val Pro Ala Pro Gln
            260                 265                 270

Val Val Ser Val Ser Val Asp Gly Ala Ser Asn Gln Pro Thr Gly Asp
```

275 280 285

Pro Ser Gly Pro Asp Gly Glu Val Glu Leu Asp Ile Glu Val Ala Gly
290 295 300

Ala Leu Ala Pro Gly Ala Lys Phe Ala Val Tyr Phe Ala Pro Asn Thr
305 310 315 320

Asp Ala Gly Phe Leu Asp Ala Ile Thr Thr Ala Ile His Asp Pro Thr
325 330 335

Leu Lys Pro Ser Val Val Ser Ile Ser Trp Gly Gly Pro Glu Asp Ser
340 345 350

Trp Thr Ser Ala Ala Ile Ala Ala Met Asn Arg Ala Phe Leu Asp Ala
355 360 365

Ala Ala Leu Gly Val Thr Val Leu Ala Ala Ala Gly Asp Ser Gly Ser
370 375 380

Thr Asp Gly Glu Gln Asp Gly Leu Tyr His Val Asp Phe Pro Ala Ala
385 390 395 400

Ser Pro Tyr Val Leu Ala Cys Gly Gly Thr Arg Leu Val Ala Ser Gly
405 410 415

Gly Arg Ile Ala Gln Glu Thr Val Trp Asn Asp Gly Pro Asp Gly Gly
420 425 430

Ala Thr Gly Gly Gly Val Ser Arg Ile Phe Pro Leu Pro Ala Trp Gln
435 440 445

Glu His Ala Asn Val Pro Pro Ser Ala Asn Pro Gly Ala Ser Ser Gly
450 455 460

Arg Gly Val Pro Asp Leu Ala Gly Asn Ala Asp Pro Ala Thr Gly Tyr
465 470 475 480

Glu Val Val Ile Asp Gly Glu Ala Thr Val Ile Gly Gly Thr Ser Ala
485 490 495

Val Ala Pro Leu Phe Ala Ala Leu Val Ala Arg Ile Asn Gln Lys Leu
500 505 510

Gly Lys Ala Val Gly Tyr Leu Asn Pro Thr Leu Tyr Gln Leu Pro Ala
515 520 525

Asp Val Phe His Asp Ile Thr Glu Gly Asn Asn Asp Ile Ala Asn Arg
530 535 540

Ala Gln Ile Tyr Gln Ala Gly Pro Gly Trp Asp Pro Cys Thr Gly Leu
545 550 555 560

Gly Ser Pro Ile Gly Val Arg Leu Leu Gln Ala Leu Leu Pro Ser Ala
565 570 575

Ser Gln Pro Gln Pro His His His His His His
580 585

<210> SEQ ID NO 3
<211> LENGTH: 364
<212> TYPE: PRT
<213> ORGANISM: artificial
<220> FEATURE:
<223> OTHER INFORMATION: activated Kumamolisin 1, backbone variant

<400> SEQUENCE: 3

Ala Ala Pro Thr Ala Tyr Thr Pro Leu Asp Val Ala Gln Ala Tyr Gln
1 5 10 15

Phe Pro Glu Gly Leu Asp Gly Gln Gly Gln Cys Ile Ala Ile Ile Glu
20 25 30

Leu Gly Gly Gly Tyr Asp Glu Ala Ser Leu Ala Gln Tyr Phe Ala Ser
35 40 45

Leu Gly Val Pro Ala Pro Gln Val Val Ser Val Ser Val Asp Gly Ala

```
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro
        355                 360


<210> SEQ ID NO 4
<211> LENGTH: 553
<212> TYPE: PRT
<213> ORGANISM: Alicyclobacillus sendaiensis

<400> SEQUENCE: 4

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60
```

```
Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Asp Gly Glu Gln Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
```

-continued

```
            485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro
545                 550


<210> SEQ ID NO 5
<211> LENGTH: 29
<212> TYPE: PRT
<213> ORGANISM: artificial
<220> FEATURE:
<223> OTHER INFORMATION: sacB signal peptide

<400> SEQUENCE: 5

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala
            20                  25
```

STABLE PROTEASE VARIANTS

CROSS REFERENCE TO RELATED APPLICATIONS

This application claims priority to U.S. application Ser. No. 16/471,507, filed Jun. 19, 2019, which claims the benefit of priority under 35 U.S.C. § 371 of International Application No. PCT/EP2017/084452, filed on Dec. 22, 2017, which claims the benefit of the filing date of European Application No. 16206367.1, filed on Dec. 22, 2016. The content of these earlier filed applications is hereby incorporated by reference herein in its entirety.

REFERENCE TO SEQUENCE LISTING

The Sequence Listing submitted herewith as a text file named "13318_0043U2_Sequence_Listing," created on Jun. 27, 2022, and having a size of 18,686 bytes is hereby incorporated by reference pursuant to 37 C.F.R. § 1.52 (e) (5).

FIELD OF THE INVENTION

The present invention relates to the field of proteases.

BACKGROUND

Proteases are today used in large array of industrial applications, including animal feed, detergents, fruit and beverage processing, leather processing, production of protein hydrolysates, hard surface cleaning or biofilm cleaning, treatment of necrotic or burned tissue to promote wound healing and/or food preparation including baking dough preparation.

In many of these applications, improved stability of the enzyme is a significant advantage. Improved thermostability helps to increase the processability of the respective protease, because the latter oftentimes undergoes thermal treatment during the manufacturing process.

This applies, inter alia, for the use of proteases in animal feed where they help to improve the digestibility and nutrient exploitation of the feed.

During feed processing, the feed is often subjected to heat, e.g., by application of steam, to reduce or eliminate pathogens, increase storage life of the feed and optimized utilization of the ingredients leading to improved feed conversion. The conditioning time can vary from a few seconds up to several minutes depending on the type and formulation of the feed. The temperature during conditioning typically ranges from 70° C. to 100° C. After conditioning, the feed is sometimes extruded through a pelleting die, which for a short time raises the temperature of the feed incrementally due to heat dissipation caused by friction.

Yet in other applications, protease enzymes are exposed to heat as well. This includes the use in detergents (e.g. exposure to hot water during laundry washing), fruit and beverage processing (heat exposure during the squeezing process or due to pasteurization or sterilization), leather processing, production of protein hydrolysates, hard surface cleaning or biofilm cleaning, treatment of necrotic or burned tissue to promote wound healing, processing aid in tissue engineering (sterilization, and denaturation of prion proteins) and/or food preparation including baking dough preparation.

Because proteases are proteins, they are susceptible to denaturation by heat and pressure. Denaturing essentially alters the structure of the enzyme, resulting in decreased activity levels and decreased efficacy of the enzyme.

There are different ways to improve protease stability or protect proteases from thermal impact. In animal feed applications, one option is Post-pellet liquid application, which is relatively complex and expensive because it requires the purchase and installation of specialized equipment, space in which to store the liquid enzyme and careful calculation of the amount of enzyme to apply.

Another option is the application of a protective coating before pelleting of the protease with other ingredients (e.g., in feed or detergents). This approach may reduce the efficacy of the enzyme because the coating may not fully dissolve, e.g., in the washing medium, or in the digestive tract of the animal. It is furthermore difficult to achieve a coating design that can withstand the high heat and moisture content of the pelleting process, but subsequently dissolve in the lower temperature and higher moisture conditions, e.g., in the animal's gut or the washing machine.

Another option is to use intrinsically thermostable proteases. These proteases are derived from thermophilic and hyper-thermophilic organisms and have unique structure and function properties of high thermostability. However, these proteases may suffer from other limitations, like suboptimal activity, specificity, bioavailability, pH-range or processability.

It is hence one object of the present invention to provide stable protease variants which do not suffer from the above discussed limitations.

SUMMARY OF THE INVENTION

These and further objects are met with methods and means according to the independent claims of the present invention. The dependent claims are related to specific embodiments.

EMBODIMENTS OF THE INVENTION

Before the invention is described in detail, it is to be understood that this invention is not limited to the particular component parts or structural features of the devices or compositions described or process steps of the methods described as such devices and methods may vary. It is also to be understood that the terminology used herein is for purposes of describing particular embodiments only, and is not intended to be limiting. The mere fact that certain measures are recited in mutually different dependent claims does not indicate that a combination of these measures cannot be used to advantage.

Any reference signs in the claims should not be construed as limiting the scope. It must be noted that, as used in the specification and the appended claims, the singular forms "a," "an" and "the" include singular and/or plural referents unless the context clearly dictates otherwise. Further, in the claims, the word "comprising" does not exclude other elements or steps.

It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

According to one embodiment of the invention, a protease variant is provided which is at least 90% identical to the full length amino acid sequence of a Kumamolisin AS backbone as set forth in any of SEQ ID NOs 1-3, or a fragment, fraction or shuffled variant thereof maintaining proteolytic activity. The protease variant demonstrates altered or improved stability compared to (i) the Kumamolisin AS wildtype as set forth in SEQ ID NO 4, or (ii) the Kumamolisin AS backbone as set forth in any of SEQ ID NOs 1-3.

The term "shuffled variant" relates to a combination of such fragment or fraction with one or more fragments from other homologous enzymes, as long as such combination maintains proteolytic activity.

The term "homologous enzyme" describes enzymes belonging to the same structural fold as Kumamolisin and at least 40% sequence identity. This category encompasses Sedolisins as discussed below herein.

Some mutants of Kumamolisin AS have been described. The discovery of N291D mutant strain of Kumamolisin AS has been discussed to providing a useful treatment against celiac disease. There are many proposals that suggest creating a genetically modified organism that could produce N291D Kumamolisin AS protein in human's gastrointestinal tracts. See US application US20140178355 A1.

Preferably, the Kumamolisin AS variant according to the invention has 93% identity, more preferably 95% identity, more preferably 98% identity, most preferably 99% identity.

The term "Kumamolisin" refers to acid proteases from the Sedolisin family of peptidases, also called S53 (MEROPS Accession MER000995, see also Wlodawer et al, 2003), comprising acid-acting endopeptidases and a tripeptidyl-peptidase. Sedolisins are endopeptidases with acidic pH optima that differ from the majority of endopetidases in being resistant to inhibition by pepstatin (Terashita et al., 1981; Oda et al., 1998).

The activation of sedolisins involves autocatalytic cleavage at pH below pH 6.5, better below pH 3.5 (see also patent application EP16176044 and Okubo et al., 2016), which releases one or more peptides to deliver the maturated and active form. Said autocatalytic cleavage is inhibited under alkaline, neutral and lightly acidic conditions.

Sedolisins comprise a catalytic triad with Glu, Asp and Ser, which in Kumamolisin AS according to SEQ ID NO 1 reside in positions Glu267, Asp271 and Ser278. The Ser residue is the nucleophile equivalent to Ser in the catalytic triad Asp, His, Ser triad of subtilisin proteases (MEROPS family S8), and the Glu of the triad is a functional substitution for the His general base in subtilisin though not in structural equivalent positions.

The protein folds of sedolisins are clearly related to that of subtilisin, and both groups are sometimes called serine proteases. However, sedolisins have additional loops. The amino acid sequences are not closely similar to subtilisins, and this, taken together with the quite different active site residues and the resulting lower pH for maximal activity, justifies the separate families.

In one embodiment, a protease variant is provided which comprises an amino acid sequence derived from a Kumamolisin AS as set forth in SEQ ID NO. 1, or a fragment, fraction or shuffled variant thereof maintaining proteolytic activity, which protease variant has one or more amino acid substitutions at one or more residue positions in SEQ ID NO. 1 selected from the group consisting of D447, A449, A517, N510, V502, E453, E360, A514, A460, A392, A386, T301, D199, Q518, G266, P553, E269, R412, S435, G320, T326, T461, Q244, D293, A487, V274, A372, K283, T308, A418, 1391, A423, A331, S327, 1219, M333, A329, N515, A378, S434, E421, A433, S230, Q393, D399, Y490, G281, Y287, R516, A475, S354, S315P, W325, L442, A470, S324, Q361, A190, T196, Q202, E228, A229, A242, D251, S262, N291, L297, H305, D306, V314, A328, 1330, L338, A342, A351, D358, G388, D402, V455, E459, A478, K483, Q497, T507, L540, Q542, A548, P551, R166 and/or D265.

Note that, while the numbering set forth above refers to SEQ ID NO 1 or 4 (which are almost identical, with 4 being the wildtype and 1 being the actual backbone used for mutagenesis, the difference between the two being the N terminal AA residue), the claimed protease can be a fragment, fraction or shuffled variant thereof maintaining proteolytic activity. In such case, the resulting amino acid sequence is shorter than that of SEQ ID NO 1 or 4, while the numbering of the mutant residues still refers to the full length SEQ ID NO 1 or 4, and has to be translated respectively to the numbering of the shorter form.

In one embodiment, the protease variant demonstrates altered or improved stability compared to (i) the Kumamolisin AS wildtype as set forth in SEQ ID NO 4, or (ii) the Kumamolisin AS backbone as set forth in any of SEQ ID NOs 1-3, In one embodiment, the protease variant has at least one amino acid substitution selected from the group consisting of D447S, A449Y, A517T, N510H, E360L, E360V, E360C, V502C, E453W, A514T, A514Y, A514D, A514S, A460W, A386I, A392V, A392L, A392I, A392M, T301S, D199E, Q518G, P553K, E269M, E269T, E269C, E269H, E269Q, G266A, D293Y, G320A, R412Q, E421R, A487Q, T461V, T461C, A331F, A331Y, A329Q, A329H, A329T, S435I, S435R, S435T, S435V, V274I, A372S, K283L, Q244C, Q244G, T308C, A418W, 1391W, A423V, T326R, T326W, T326L, T326K, I219L, S327F, S327L, S327W, M333I, N515G, A378G, S434G, A433G, S230D, Q393S, D399S, Y490W, A190D, T196S, Q202D, E228Q, A229W, A242S, D251S, S262C, G281R, Y287K, N291T, N291S, D293F, L297T, T301C, T301M, H305F, H305W, D306S, V314M, V314L, S315P, G320Q, G320S, S324L, S324R, W325K, A328W, A328D, A328R, A328Y, 1330L, M333Y, M333L, L338R, A342R, A351S, S354E, S354Q, D358G, Q361C, Q361L, A386L, A386V, A386M, G388C, D402E, R412M, R412E, R412D, L442W, L442W, D447C, D447A, A449L, A449M, A449E, A449N, E453Y, E453F, V4551, V455L, E459W, A460R, A470V, A475V, A478L, K483A, Q497Y, Q497M, Q497D, Q497R, V502T, T507L, R516L, R516E, R516I, A517S, L540V, Q542H, Q542D, Q542S, A548S, P551N, P551R, P553L, R1661, D265T, compared to the Kumamolisin as as set forth in SEQ ID NO 1 or 4.

These individual amino acid substitutions are shown in Table 1. Note that, while the numbering set forth above refers to SEQ ID NO 1 or 4, the claimed protease can be a fragment, fraction or shuffled variant thereof maintaining proteolytic activity. In such case, the resulting amino acid sequence is shorter, or longer, than that of SEQ ID NO 1 or 4, while the numbering of the mutant residues still refers to the full length SEQ ID NO 1 or 4.

In one embodiment of the invention, the protease variant has at least one amino acid substitution compared to the Kumamolisin AS as set forth in SEQ ID NO 1 or 4, which substitution is selected from the group consisting of:

A517T or A517S
A514S, A514T or A514D
N510H
V502C
A449Y, A449N or less preferred A449E
D447S or D447C.
A3921, A392L, A392V or A392M
E360L, E360V or E360C
E269H, E269T, E269M, E269C or E269Q
Q518G
G320Q, G320A or less preferred G320S
A386I, A386L, A386V or A386M
G266A
A372S
E453Y, E453W or less preferred E453F
A460W
A329Q, A329H or A329T.
D293Y
R412E, R412D, R412Q or R412M
T301S
D199E
A331F or A331Y
S435T, S435R or S435I
V274I
D399S
S230D
S434G
M3331 or M333L
N515G
A418W
1391W
E421R
A487Q
A378G
A423V
T326K, T326L, T326 R or T326W
A433G
D399S
Y490W
R516E or R516I
P553K
V314L
S327W, S327L or S327FA475V
A342R
S354E or S354Q
S315P Some of these substitutions cause a high ΔIT50 when introduced individually into the Kumamolisin AS as set forth in SEQ ID NO 1 or 4, and are therefore preferred, while others have a high occurrence in the combinatorial and distinct clones of Tables 2a, 2b and 4 and some combinations, which have a combination of individual substitutions with a high overall ΔIT50.

Some can interchangeably be used to stabilize the enzyme and some combinations results in other traits that are relevant for the production or performance in feed, like fermentation titers, the hydrolysis of anti-nutritive factors as protease inhibitors (soy bean Bowman-Birk and Kunitz-type trypsin and/or chymotrypsin inhibitors), pH profile, pH and pepsin stability, or stability against and performance under higher ionic strength.

Note that, while the numbering set forth above refers to SEQ ID NO 1 or 4, the claimed protease can be a fragment, fraction or shuffled variant thereof maintaining proteolytic activity. In such case, the resulting amino acid sequence is shorter than that of SEQ ID NO 1 or 4, while the numbering of the mutant residues still refers to the full length SEQ ID NO 1 or 4.

In one embodiment of the invention, the protease variant has at least two amino acid substitutions compared to the Kumamolisin AS backbone as set forth in SEQ ID NO 1 or 4. Preferably the protease variant has at least three, more preferably at least four, more preferably at least five and most preferably at least six amino acid substitutions selected from said group. Preferably, these amino acid substitutions are combinations of the individual substitutions discussed above.

In one embodiment of the invention, the protease variant has at least two amino acid substitutions compared to the Kumamolisin AS backbone as set forth in SEQ ID NO 1 or 4, the at least 2 amino acid substitutions being at two or more residue positions in SEQ ID NO 1 or 4 selected from the group consisting of 447 and 449, 453, 502, 510, 517, 360, 460, 199, 266, 301, 386 and 514. Preferably the protease variant has at least three, more preferably at least four, more preferably at least five and most preferably at least six amino acid substitutions selected from said group.

In one preferred embodiment, the protease variant has at least one, preferably at least two, more preferably at least three, more preferably at least four, more preferably at least five, most preferably at least six amino acid substitutions selected from the group consisting of D447S, A449Y, A517T, N510H, E360L, E360V, E360C, V502C, E453W, A514T, A514Y, A460W, A386I, D199E, G266A, T301S.

Tables 2a, 2b and 4 show sets of such so-called "distinct clones" or "combinatorial clones" which have combinations of the individual mutations set forth above.

As used herein, the term "combinatorial clone or variant" means a clone or variant screened from a recombination library. Such a recombination library contains a population carrying different amounts and mutations selected from the group of table 1.

As used herein, the term "distinct clone or variant" means A clone constructed containing a defined set of mutations selected from the group of table 1 in a rational approach.

Preferably, said improved stability which the protease variant according to the invention has is improved thermostability (IT50). The thermostability of an enzyme is usually determined by measuring the inactivation temperature (IT 50). The "inactivation temperature" is defined as the temperature at which the residual activity of the enzyme after incubation for a certain duration and subsequent cooling to room temperature is 50% of the residual activity of the same enzyme incubated for the same duration under the same conditions at room temperature.

According to one embodiment, the protease variant has a set of substitutions at selected residues in the Kumamolisin AS backbone as set forth in SEQ ID NO 1 or 4, which set is at least one of the following a) 360, 447, 449 and 510
b) 447, 449 and 514, and/or
c) 447, 449, 453, and 517.

These three sets of simultaneously substituted residues occur in three sets of specific distinct or combinatorial clones which are particularly preferred (consensus mutations). See Table 2a/FIG. 3, Table 2b/FIG. 4 and Table 4/FIG. 5. For these reasons, these sets of simultaneously substituted residues seem to be particularly synergistic when it comes to improvement of stability.

According to one embodiment said improved stability is improved thermostability (IT50) of either the activated enzyme or the zymogen. In one embodiment of, the protease variant has an IT50 of between ≥75 and ≤105° C.

In some embodiments, for the activated enzyme an IT50 of between ≥70 and ≤90° C. is provided, while a for the zymogen an IT50 of between ≥80 and ≤105° C. is provided.

The Kumamolisin AS wildtype enzyme has an IT50 of 79.6° C.+/−0.4° C. (n=46) as the zymogen, i.e., the inactive zymogen, and an IT50 of 59° C.+/−1° C. (n=10) as the activated enzyme. In the course of this specification, the different variants are either characterized by their IT50, or by ΔIT50 (i.e., the difference compared to the wildtype IT50).

According to another embodiment of the invention, a nucleic acid molecule encoding a protease variant according the above description is provided. Furthermore, a plasmid or vector system comprising said nucleic acid molecule is provided, as well as a host cell being transformed with said plasmid or vector and/or comprising said nucleic acid molecule is provided.

Further, a method for producing a protease or protease variant is provided, said method encompassing:

a) cultivating said host cell, and
b) isolating the protease or protease variant from said host cell, or harvesting the protease or protease variant from the medium.

According to another embodiment of the invention, a composition comprising a protease variant according to the above description is provided, which composition has a pH of ≥5.

Such composition is generally discussed-yet not with the specific protease variants disclosed herein—in EP Application Serial No. 16176044.2-1375 and later applications claiming the priority thereof, the content of which is incorporated by reference herein.

According to another embodiment of the invention, a feed additive, feed ingredient, feed supplement, and/or feedstuff comprising a protease variant or a composition according to the above description is provided.

Further, the use of a protease variant according to the above description for the manufacture of a feedstuff is provided.

Such feed additive, feed ingredient, feed supplement, and/or feedstuff is preferably meant for monogastric poultry, pig, fish and aquaculture, where it helps to increase protein digestion and absorbance from the feedstuff, plus degrade proteinogenic compounds which are detrimental for animal health or digestion.

Furthermore, the use of a protease according to the above description is provided for at least one purpose or agent selected from the group consisting of:

detergent
fruit and beverage processing
leather processing
production of protein hydrolysates
hard surface cleaning or biofilm cleaning
treatment of necrotic or burned tissue to promote wound healing,
processing aid in tissue engineering and/or
food preparation including baking dough preparation.

Likewise, an additive, ingredient or agent for one purpose or agent selected from the group consisting of:

detergent
fruit and beverage processing
leather processing
production of protein hydrolysates
hard surface cleaning or biofilm cleaning
treatment of necrotic or burned tissue to promote wound healing
processing aid in tissue engineering and/or
food preparation including baking dough preparation.
is provided which additive, ingredient or agent comprises a composition according to the above description.

Furthermore, a process of generating a protease variant according to the above description is provided, which process comprises:

i) mutagenizing a DNA, cDNA or mRNA encoding a Kumamolisin AS amino acid sequence as set forth in any of SEQ ID NOs 1-4
ii) expressing one or more mutants of Kumamolisin AS thus obtained, and
iii) testing the one or more mutants of Kumamolisin AS for at least stability, preferably thermostability.

Preferably, in said method, the encoding nucleic acid sequence and/or the amino acid sequence of one or variants of Kumamolisin AS is determined. For this purpose, routine methods from the prior art can be used.

EXPERIMENTS AND FIGURES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Any reference signs should not be construed as limiting the scope.

All amino acid sequences disclosed herein are shown from N-terminus to C-terminus; all nucleic acid sequences disclosed herein are shown 5'→3'.

1. Amino Acid Sequences of the Kumamolisin AS Backbone

SEQ ID NO:1 shows the proenzyme (propeptide plus enzyme, also called zymogen herein) sequence of the Kumamolisin AS backbone used herein. It is important to understand that, while the wildtype sequence of Kumamolisin AS has an N-terminal M residue, the Kumamolisin AS backbone used herein lacks said M, because the latter was replaced by a signal sequence that was later cleaved off. Such signal sequence is for example, the sacB signal peptide MNIKKFAKQATVLTFTTA LLAGGATQAFA (SEQ ID NO:5).

In SEQ ID NO: 1, the propeptide hence comprises AAs 2-189 (former N-terminal M which is lacking is yet considered as AA NO 1 in the numbering of SEQ ID NO), and the enzyme comprises AAs 190-553:

```
SDMEKPWKE GEEARAVLQG HARAQAPQAV DKGPVAGDER MAVTVVLRRQ RAGELAAHVE    60

RQAAIAPHAR EHLKREAFAA SHGASLDDFA ELRRFADAHG LALDRANVAA GTAVLSGPVD   120

AINRAFGVEL RHFDHPDGSY RSYLGEVTVP ASIAPMIEAV LGLDTRPVAR PHFRMQRRAE   180
```

-continued

```
GGFEARSQAA APTAYTPLDV AQAYQFPEGL DGQGQCIAII ELGGGYDEAS LAQYFASLGV   240

PAPQVVSVSV DGASNQPTGD PSGPDGEVEL DIEVAGALAP GAKFAVYFAP NTDAGFLDAI   300

TTAIHDPTLK PSVVSISWGG PEDSWTSAAI AAMNRAFLDA AALGVTVLAA AGDSGSTDGE   360

QDGLYHVDFP AASPYVLACG GTRLVASGGR IAQETVWNDG PDGGATGGGV SRIFPLPAWQ   420

EHANVPPSAN PGASSGRGVP DLAGNADPAT GYEVVIDGEA TVIGGTSAVA PLFAALVARI   480

NQKLGKAVGY LNPTLYQLPA DVFHDITEGN NDIANRAQIY QAGPGWDPCT GLGSPIGVRL   540

LQALLPSASQ PQP                                                      553
```

The propeptide is in bold. The catalytic triad SED (=Ser/Glu/Asp) consists of E267, D271 and S467, shown in italics. The positions where the inventors have found mutations that result in altered/improved properties are underlined.

2. Amino Acid Sequences of the Kumamolisin AS Backbone Plus Leader Sequence and HisTag In SEQ ID NO:2, the sacB leader sequence comprises AAs 1-29 (wavy underline) and replaces the original N-terminal M of the propeptide. The propeptide (bold) comprises AA 30-217, the activated enzyme comprises AA 218-581 and the His-tag comprises AAs 582-587 (double underline).

```
MNIKKFAKQA TVLTFTTALL AGGATQAFAS DMEKPWKEGE EARAVLQGHA RAQAPQAVDK    60

GPVAGDERMA VTVVLRRQRA GELAAHVERQ AAIAPHAREH LKREAFAASH GASLDDFAEL   120

RRFADAHGLA LDRANVAAGT AVLSGPVDAI NRAFGVELRH FDHPDGSYRS YLGEVTVPAS   180

IAPMIEAVLG LDTRPVARPH FRMQRRAEGG FEARSQAAAP TAYTPLDVAQ AYQFPEGLDG   240

QGQCIAIIEL GGGYDEASLA QYFASLGVPA PQVVSVSVDG ASNQPTGDPS GPDGEVELDI   300

EVAGALAPGA KFAVYFAPNT DAGFLDAITT AIHDPTLKPS VVSISWGGPE DSWTSAAIAA   360

MNRAFLDAAA LGVTVLAAAG DSGSTDGEQD GLYHVDFPAA SPYVLACGGT RLVASGGRIA   420

QETVWNDGPD GGATGGGVSR IFPLPAWQEH ANVPPSANPG ASSGRGVPDL AGNADPATGY   480

EVVIDGEATV IGGTSAVAPL FAALVARINQ KLGKAVGYLN PTLYQLPADV FHDITEGNND   540

IANRAQIYQA GPGWDPCTGL GSPIGVRLLQ ALLPSASQPQ PHHHHHH   587
```

3. Amino Acid Sequences of the Activated Kumamolisin AS Backbone Devoid of Propeptide In SEQ ID NO:3, the activated Kumamolisin AS backbone enzyme is shown with AAs 1-364:

```
AAPTAYTPLD VAQAYQFPEG LDGQGQCIAI IELGGGYDEA SLAQYFASLG VPAPQVVSVS    60

VDGASNQPTG DPSGPDGEVE LDIEVAGALA PGAKFAVYFA PNTDAGFLDA ITTAIHDPTL   120

KPSVVSISWG GPEDSWTSAA IAAMNRAFLD AAALGVTVLA AAGDSGSTDG EQDGLYHVDF   180

PAASPYVLAC GGTRLVASGG RIAQETVWND GPDGGATGGG VSRIFPLPAW QEHANVPPSA   240

NPGASSGRGV PDLAGNADPA TGYEVVIDGE ATVIGGTSAV APLFAALVAR INQKLGKAVG   300

YLNPTLYQLP ADVFHDITEG NNDIANRAQI YQAGPGWDPC TGLGSPIGVRL LQALLPSAS  360

QPQP                                                                364
```

4. Amino Acid Sequence of the Kumamolisin AS Wildtype

SEQ ID NO:4 shows the proenzyme (propeptide plus enzyme) sequence of the Kumamolisin AS wildtype, as obtained from *Alicyclobacillus sendaiensis* (GenBank: AB085855.1). SEQ ID NO:4 differs from SEQ ID NO:1, which shows the sequence of the Kumamolisin AS backbone used herein in that the latter lacks the N-terminal M still present in the Wildtype SEQ ID NO:4. This is because the N-terminal M was replaced, in SEQ ID NO:1, by the sacB signal sequence, which was later cleaved off. In SEQ ID NO:4, the propeptide comprises AAs 1-189, and the enzyme comprises AAs 190-553:

MSDMEKPWKE GEEARAVLQG HARAQAPQAV DKGPVAGDER MAVTVVLRRQ RAGELAAHVE 60

RQAAIAPHAR EHLKREAFAA SHGASLDDFA ELRRFADAHG LALDRANVAA GTAVLSGPVD 120

AINRAFGVEL RHFDHPDGSY RSYLGEVTVP ASIAPMIEAV LGLDTRPVAR PHFRMQRRAE 180

GGFEARSQAA APTAYTPLDV AQAYQFPEGL DGQGQCIAII ELGGGYDEAS LAQYFASLGV 240

PAPQVVSVSV DGASNQPTGD PSGPDG*E*VEL *D*IEVAGALAP GAKFAVYFAP NTDAGFLDAI 300

TTAIHDPTLK PSVVSISWGG PEDSWTSAAI AAMNRAFLDA AALGVTVLAA AGDSGSTDGE 360

QDGLYHVDFP AASPYVLACG GTRLVASGGR IAQETVWNDG PDGGATGGGV SRIFPLPAWQ 420

EHANVPPSAN PGASSGRGVP DLAGNADPAT GYEVVIDGEA TVIGGTSAVA PLFAALVARI 480

NQKLGKAVGY LNPTLYQLPA DVFHDITEGN NDIANRAQIY QAGPGWDPCT GLGSPIGVRL 540

LQALLPSASQ PQP 553

Again, the propeptide is in bold. The catalytic triad SED (=Ser/Glu/Asp) consists of E267, D271 and S467, shown in italics.

SHORT DESCRIPTION OF THE FIGURES

EXAMPLE 1: PROTEASE ACTIVITY ASSAY

Figure 1:
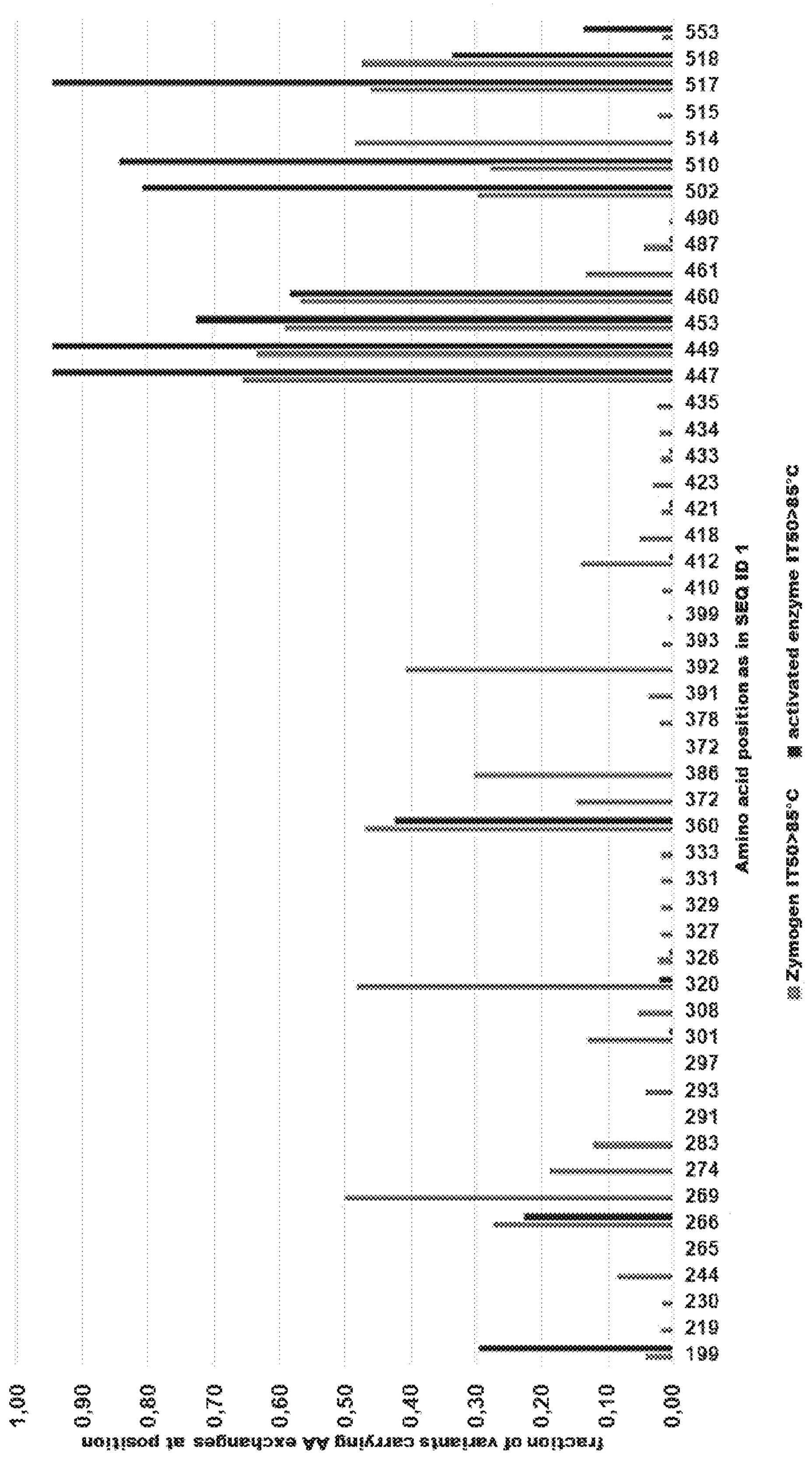
FIG. 1 shows the distribution of mutations in variants optimized for thermal stability of the zymogen and the activated enzyme.

Protease activity assays were carried out in microtiter plates a) AAPF Assay 96 Well Formate Assay buffer: 200 mM Sodium Acetate, 1 mM $CaCl_2$, 0.01% Triton X-100 at pH 3 depending on the experiment Substrate stock solution: 100 mM in water free DMSO Substrate working solution: Substrate Stock solution diluted 1:50 in assay buffer, Execution: Load 50 μL of the diluted sample into the wells of a Nunc 96 clear flat bottom plate. Dilution is made in water containing 0.01% Triton-X100 corresponding to the volumetric activity of the sample. Start reaction by adding 50 μL of substrate working solution. Measure kinetics at 37° C. by monitoring the increase in adsorption at 410 nm as a measure for enzymatic activity. The activity was calculated by building a calibration curve with a reference enzyme preparation of the backbone with known proteolytic activity measured by a reference method.

For assaying the protease activity at different pH values the following buffers were used, each 200 mM: glycine/HCL between pH 2.0-3.0, trisodium citrate/citric acid between 3.0 and 6.0 and Tris/maleic acid between 6.0 and 7.5.

b) $IT_{50}$ $IT_{50}$ defines the temperature where 50% of the activity is inactivated under the conditions described above. Although not equivalent to, it is a measure for the thermal stability in the application, e.g. pelleting conditions or conditions in a detergent application, either dish washing or the cleaning of a fabric or hard surface and other technical applications.

The screening of enzyme variants under predictive conditions is essential. For proteases like those described herein, screening for thermally more stable variants by methods as also described herein can be affected by the self-hydrolysis of the protease. As already described in patent application EP16176044 Example 9, screening for variants with higher thermal stability under conditions where the protease is active results in a large number of false positives, as the result of a mixed effect of thermal inactivation and self-hydrolysis. The same applications teaches to circumvent this problem in the absence of small molecule reversible enzyme inhibitors, as is the case for the class of acid protease described herein, by executing the test for thermal stability of the enzyme and enzyme variants in the form of the inactive enzyme zymogen in the way described below.

Assay buffers: 50 mM sodium phosphate, 0.25 mM $CaCl_2$ pH6.5 800 mM glycine/HCl pH2.8

Thermal inactivation execution: Samples were diluted corresponding to the volumetric activity in potassium phosphate buffer. The pH of the final solution was checked to be above pH 6.3. The samples were transferred in replicates, 20 μL per well, into a 384 well PCR plate according to the direction of the temperature gradient of the PCR machine. The plates were sealed with an adhesive or hot melting cover foil and incubated on a thermal gradient cycler with a temperature gradient of +/−12° C. around the expected IT50 value for 10 minutes. The samples were cooled to 8° C. before measuring the residual activity of the samples with AAPF-pNA as followed. Samples, 15 μL each from the temperature incubation plate were transferred into a 384 well greiner clear flat bottom PS-microplate and 9 μL of glycine buffer was added to activate the protease during an incubation of 1 hour at 37° C. After the activation of the protease the assay was started by adding 24 μL of an AAPF-pNA solution (2 mM AAPF-pNA in water with 0.01% Triton-X100) and activity was measured by following the kinetics at 37° C. The normalized experimental data for residual activity at the inactivation temperatures were fitted to a four parameter logistics function to evaluate the IT50.

c) IT50 without propeptide-activated enzyme protein:

Enzyme activation prior to thermal inactivation execution. Samples were diluted corresponding to the volumetric activity in glycine buffer pH 2.8 as described in 2b) and pH was checked to be equal or lower than pH 4.0. Samples were activated by an incubation for 1 hour at 37° C. After the incubation pH was set to above 7.0 by diluting the samples 1:3 in 50 mM sodium phosphate buffer pH 8.0. Thermal inactivation of activated enzyme protein execution. Aliquots of the activated enzyme protein were transferred in replicates, 20 μL per well, into a 384 well PCR plate according to the direction of the temperature gradient of the PCR machine. The plates were sealed with an adhesive or hot melting cover foil and incubated on a thermal gradient cycler with a temperature gradient of +/−12° C. around the expected IT50 value for 10 minutes. The samples were cooled to 8° C. before measuring the residual activity of the samples with AAPF-pNA as followed. Samples, 15 μL each from the temperature incubation plate were transferred into a 384 well greiner clear flat bottom PS-microplate and 9 μL of glycine/HCl buffer was added to adjust the pH to 3.0. The assay was started by adding 24 μL of an AAPF-pNA solution (2 mM AAPF-pNA in water with 0.01% Triton-X100) and activity was measured by following the kinetics at 37° C. The normalized experimental data for residual activity at the inactivation temperatures were fitted to a four parameter logistics function to evaluate the IT50.

d) pH-Profile—Activated Enzyme Protein

Undiluted bacterial supernatant containing enzyme protein was titrated with 1 M HCl to pH 4 and enzyme was activated at 37° C. for 60 min. 20 μL of sample were added to 200 μL Britton Robinson buffer with pH 1.8-7.0 (adjusted to conductivity of 15 mS/cm with NaCl). 20 μL were then transferred into a 384-well Greiner flat bottom PS-microplate plus 20 μl substrate solution (2 mM AAPF-pNA in water with 0.01% Triton-X100) and activity was measured by monitoring the kinetics at 410 nm and 37° C. as described in example 1a). Each kinetic experiment was run in quadruplet.

e) pH/Pepsin-Resistance

Undiluted bacterial supernatant containing enzyme protein was titrated with 1 M HCl to pH 2.5. 90 μl were then transferred to a Nunc 96-well clear flat bottom microtiter plate. 10 μl of a 250 μg/mL Pepsin stock solution in pH 2.5 buffer (final concentration in assay 25 μg/mL) or pH 2.5 buffer were added to each well and then incubated at 37° C. for 30 min. Finally, 5 μl of a 100 μM Pepstatin A solution (final concentration 5 μM) was added to each well to stop the pepsin reaction. 25 μl of the sample were transferred in 175 μl glycine/HCl buffer pH 3.0 in a new Nunc 96-well clear flat bottom microtiter plate. 20 μl were then transferred into a 384-well Greiner flat bottom PS-microplate plus 20 μl substrate solution (2 mM AAPF-pNA in water with 0.01% Triton-X100) and activity was measured by monitoring the kinetics at 410 nm and 37° C. as described in example 1 a). Each kinetic experiment was run in quadruplet.

f) Conductivity Dependency

20 μl undiluted bacterial supernatant was diluted in 180 μL glycine/HCl buffer pH 3.0 adjusted with NaCl to conductivity of 2, 4, 6, 10, 20, 30, 40, 50 mS/cm in a Nunc 96-well clear flat bottom microtiter plate. The samples were incubated at 37° C. for 20 min and then 20 μL sample were then transferred into a 384-well Greiner flat bottom PS-microplate plus 20 μl substrate solution (2 mM AAPF-pNA in water with 0.01% Triton-X100) and activity was measured by monitoring the kinetics at 410 nm and 37° C. as described in example 1 a). Each kinetic experiment was run in quadruplet.

g) BBI/KTI Hydrolysis—Functional Trypsin Assay

Bowman-Birk and Kunitz-type inhibitors (BBI/KTI) are strong inhibitors of serine proteases which are widely spread in seed of legumes and cereal grains. The assay principle is that a proteolytic degradation of the BBI/KTI by protease activity recovers the natural trypsin activity on Benzyl-Arginine-pNA (Bz-R-pNA) substrate without inhibitors. 90 μL of bacterial supernatant containing enzyme protein was diluted in glycine/HCl buffer to pH 3.0 and then incubated at 37° C. for 30 min. 20 μl of the sample was then mixed with 20 μl inhibitor solution (KTI: 8 μg/mL; BBI: 16 μg/mL; KTI/BBI: 4/8 μg/mL diluted in glycine buffer pH 3.0) and further incubated at 37° C. for 60 min. 15 μl of the sample were transferred into a 384-well Greiner flat bottom PS-microplate and then 15 μl trypsin solution in pH 8.0 (final trypsin concentration 1 μg/mL; final pH 7.0 or pH 7.5) was added to each well and the plate was incubated at 37° C. for 10 min. Finally, 30 μL substrate solution (2 mM Bz-R-pNA in water with 0.01% Triton-X100) was added to each well and activity was measured by monitoring the kinetics at 410 nm and 37° C. as described in example 1 a). Each kinetic experiment was run in quadruplet.

EXAMPLE 2: GENERATION OF GENETIC DIVERSITY

Initial genetic diversity was introduced by randomizing each position of the active enzyme core sequence of SEQ ID NO 1. Mutant enzyme single site saturation libraries were introduced in the gene carried on an *E. coli/Bacillus* shuttle vector using mutagenesis methods as described in Green & Sambrook (eds), Molecular Cloning, 4th edition, CSHL and suitable mutagenic PCR methods as disclosed in Cadwell and Joyce (PCR Methods Appl. 3 [194], 136-140. Protease enzyme variants were characterized after heterologous expression in *Bacillus subtilis* and phenotypically optimized variants selected by the screening procedure outlined in Example 3.

In general, methods to mutagenize a protein, like an enzyme, to obtain a library of mutated proteins members of which may have altered characteristics, are well established. Methods to mutagenize a protein encompass site directed mutagenesis and others, as described e.g. in Hsieh & Vaisvila (2013), content of which incorporated herein by reference for enablement purposes.

Such methods are sometimes called "directed evolution", namely when the established library is then screened for particular features. Packer & Liu (2015) provide an overview of the respective methodology, content of which incorporated herein by reference for enablement purposes.

EXAMPLE 3: PHENOTYPICALLY SCREENING FOR ENZYME VARIANTS WITH INCREASED THERMAL STABILITY

The generated genetic diversity either in the initial stage in form of single site saturation libraries or in the subsequent stage in the form of recombination libraries or distinct clones was screened for variants with an optimized phenotype, i.e. increased thermal stability using the method as described in example 1b) with adaptations required to run them in a fully automated robotic workstation at high throughput. These were mainly adaptation in incubation times, volumes, substrate and the main adaptation was to select optimized variants not by the thermal inactivation profile on a temperature gradient but by the residual activity after incubation at a single temperature, the temperature which was set to discriminate optimized variants from the average of the genetic diversity. Protease variants were derived which differed in one or more amino acid positions from SEQ ID NO 2, including two positions, three positions, n positions. Appropriate iterative rounds of the procedures described herein were performed to satisfy the demands of the application

EXAMPLE 4

The following individual mutations which increase the IT50 compared to the used backbone were identified. The IT50 was analyzed as described above and compared to the IT50 of the used backbone (=wildtype with missing N-terminal methionine) characterizing the variant by the corresponding ΔIT50. The backbone has an IT50 of 79.6° C.+/−0.4° C. (n=46) as zymogen and an IT50 of 59° C.+/−1° C. (n=10) as activated enzyme.

TABLE 1

Kumamolisin AS single amino acid substitutions relative to SEQ ID NO 1. and their ΔIT 50 compared to the backbone for the zymogen and the activated enzyme

| Position | Mutation | ΔIT 50 Zymogen | ΔIT 50 activated Enzyme |
|---|---|---|---|
| A190 | D | 1.5 | 0.8 |
| T196 | S | 0.7 | 0.3 |
| D199 | E | 0.5 | 1.0 |
| Q202 | D | 0.4 | −0.3 |
| 1219 | L | 1.1 | 0.8 |
| E228 | Q | 0.7 | 0.1 |
| A229 | W | 0.2 | n.d. |
| S230 | D | 2.8 | −0.8 |
| A242 | S | 0.3 | −0.4 |
| Q244 | C | 0.5 | −3.6 |
| Q244 | G | 0.7 | 1.5 |
| D251 | S | 0.8 | −0.3 |
| S262 | C | 0.9 | −0.3 |
| G266 | A | 1.7 | 0.0 |
| E269 | M | 2.4 | −o.i |
| E269 | T | 2.6 | −o.i |
| E269 | c | 2.1 | −1.1 |
| E269 | H | 4.0 | −0.5 |
| E269 | Q | 2.0 | −1.4 |
| V274 | 1 | 1.8 | 1.3 |
| G281 | R | 2.0 | 5.4 |
| K283 | L | 0.6 | −0.2 |
| Y287 | K | 0.2 | 5.2 |
| N291 | T | 0.7 | 0.5 |
| N291 | s | −0.2 | 1.0 |
| D293 | Y | 0.8 | 1.0 |
| D293 | F | 1.1 | 1.3 |
| L297 | T | 1.2 | 0.2 |
| T301 | s | 0.6 | 7.6 |
| T301 | c | 0.8 | 1.0 |
| T301 | M | 0.7 | 0.5 |
| H305 | F | 0.4 | −0.4 |
| H305 | W | 0.1 | −2.7 |
| D306 | S | 0.3 | −0.5 |
| T308 | C | 0.5 | −0.8 |
| V314 | M | 0.6 | 0.3 |
| V314 | L | 2.5 | 0.7 |
| S315P | P | 0.8 | 3.0 |
| G320 | A | 3.0 | −0.2 |
| G320 | Q | 3.6 | 1.5 |
| G320 | S | 1.0 | 0.6 |
| S324 | L | 0.1 | 1.3 |
| S324 | R | 0.7 | 2.0 |
| W325 | K | −0.3 | 2.7 |
| T326 | R | 1.7 | 1.2 |
| T326 | W | 0.9 | 0.2 |
| T326 | L | 1.7 | 1.6 |
| T326 | K | 1.9 | 1.2 |
| S327 | F | 1.2 | 0.6 |
| S327 | L | 1.5 | 1.1 |
| S327 | W | 2.0 | 1.0 |
| A328 | W | 0.6 | 0.5 |
| A328 | D | 1.3 | 1.1 |
| A328 | R | 1.1 | 0.1 |
| A328 | Y | 1.5 | 0.8 |
| A329 | Q | 2.8 | 0.2 |
| A329 | H | 2.1 | 0.3 |
| A329 | T | 1.0 | 0.9 |

TABLE 1-continued

Kumamolisin AS single amino acid substitutions relative to SEQ ID NO 1. and their ΔIT 50 compared to the backbone for the zymogen and the activated enzyme

| Position | Mutation | ΔIT 50 Zymogen | ΔIT 50 activated Enzyme |
|---|---|---|---|
| 1330 | L | 1.1 | 0.8 |
| A331 | F | 2.0 | 0.6 |
| A331 | Y | 1.3 | 0.6 |
| M333 | 1 | 2.5 | −0.7 |
| M333 | Y | 0.3 | 1.0 |
| M333 | L | 2.4 | −i.o |
| L338 | R | −0.5 | 1.5 |
| A342 | R | −0.6 | 3.9 |
| A351 | S | 1.3 | −0.9 |
| S354 | E | 1.6 | 3.3 |
| S354 | Q | 2.0 | 0.3 |
| D358 | G | −2.0 | 0.7 |
| E360 | L | 1.4 | 3.1 |
| E360 | V | 2.4 | 2.9 |
| E360 | C | 2.3 | 2.3 |
| Q361 | C | 0.9 | 1.5 |
| Q361 | L | 0.2 | 0.1 |
| A372 | S | 2.4 | −0.7 |
| A378 | G | 1.5 | 1.5 |
| A386 | 1 | 3.6 | 0.5 |
| A386 | L | 2.7 | 1.3 |
| A386 | V | 2.1 | 1.2 |
| A386 | M | 1.7 | 0.0 |
| G388 | C | 0.6 | −3.5 |
| 1391 | W | 1.7 | 0.6 |
| A392 | V | 2.8 | 0.7 |
| A392 | L | 3.0 | 0.9 |
| A392 | 1 | 3.7 | 2.4 |
| A392 | M | 2.3 | 2.0 |
| Q393 | S | 0.9 | 0.2 |
| D399 | S | 2.3 | 2.1 |
| D402 | E | 0.6 | 1.7 |
| 412 | Q | 0.5 | 2.4 |
| R412 | M | 1.5 | 2.9 |
| R412 | E | 1.8 | 4.4 |
| R412 | D | 0.4 | 3.5 |
| A418 | W | 2.8 | 0.2 |
| E421 | R | 1.0 | 0.5 |
| A423 | V | 1.1 | 0.8 |
| A433 | G | 1.4 | 1.9 |
| S434 | G | 1.9 | 0.7 |
| S435 | 1 | 1.7 | 1.6 |
| S435 | R | 1.8 | 0.5 |
| S435 | T | 2.5 | 4.7 |
| S435 | V | 1.6 | 2.1 |
| L442 | w | 1.4 | 0.3 |
| L442 | w | −0.7 | 2.4 |
| D447 | s | 4.0 | 3.2 |
| D447 | c | 3.0 | 1.4 |
| D447 | A | 1.6 | 1.3 |
| A449 | Y | 1.7 | 0.7 |
| A449 | L | 0.8 | 0.3 |
| A449 | M | 1.9 | −0.9 |
| A449 | E | 1.6 | 0.4 |
| A449 | N | 1.6 | 3.3 |
| E453 | W | 2.4 | 0.0 |
| E453 | Y | 2.6 | 0.7 |
| E453 | F | 1.1 | -0.5 |
| V455 | 1 | 1.2 | 0.3 |
| V455 | L | 1.8 | 0.7 |
| E459 | W | 0.9 | -0.3 |
| A460 | W | 2.6 | 0.5 |
| A460 | R | 2.0 | −0.6 |
| T461 | V | 1.2 | 0.0 |
| T461 | C | 1.2 | 0.6 |
| A470 | V | 0.6 | 2.3 |
| A475 | V | −0.3 | 3.7 |
| A478 | L | 1.2 | 0.2 |
| K483 | A | 1.5 | 0.7 |
| A487 | Q | 0.0 | 1.6 |
| Y490 | W | 1.5 | 0.3 |
| Q497 | Y | 1.8 | 1.2 |

TABLE 1-continued

| Kumamolisin AS single amino acid substitutions relative to SEQ ID NO 1. and their ΔIT 50 compared to the backbone for the zymogen and the activated enzyme | | | |
|---|---|---|---|
| Position | Mutation | ΔIT 50 Zymogen | ΔIT 50 activated Enzyme |
| Q497 | M | 0.8 | 0.8 |
| Q497 | D | 0.3 | 1.0 |
| Q497 | R | 0.6 | 0.2 |
| V502 | C | 2.3 | 1.9 |
| V502 | T | 1.5 | 1.6 |
| T507 | L | 0.2 | 1.0 |
| N510 | H | 2.4 | 7.9 |
| A514 | T | 2.2 | 1.3 |
| A514 | Y | 1.3 | −1.2 |
| A514 | D | 1.5 | 1.2 |
| A514 | S | 2.4 | 0.5 |
| N515 | G | 2.0 | −0.2 |
| 516 | L | 0.5 | 1.2 |
| R516 | E | 1.1 | 3.5 |
| R516 | 1 | 1.2 | 4.3 |
| A517 | T | 1.3 | 3.9 |
| A517 | s | 0.3 | 7.7 |
| Q518 | G | 1.6 | 4.1 |
| L540 | V | 0.7 | 0.5 |
| Q542 | H | 0.9 | −0.2 |
| Q542 | D | 1.1 | 0.4 |
| Q542 | S | 0.4 | 0.5 |
| A548 | S | 0.2 | n.d. |
| P551 | N | 0.9 | −0.4 |
| P551 | R | 0.6 | 0.3 |
| P553 | K | 0.5 | 0.3 |
| P553 | L | 0.8 | 0.2 |
| R166 | 1 | 1.0 | 0.7 |
| D265 | T | 1.7 | n.d. |

Quite a few distinct clones and combinatorial clones as shown in Table 3 have substitutions in these positions, leading to synergistic effects in thermal stabilization, when two or more residues thereof are mutated simultaneously.

EXAMPLE 5

Distinct variants were generated by introducing selected distinct mutations into the Kumamolisin AS wild-type sequence via site-directed mutagenesis. Suitable mutagenic PCR methods known in the art and standard cloning techniques as described in Green & Sambrook (eds), Molecular Cloning, $4^{th}$ edition, CSHL were used. Protease enzyme variants were characterized after heterologous expression in *Bacillus subtilis* and phenotypically analysis using the methods described above.

Combinatorial libraries, combining mutations identified in the examples provided above and outlined in Table 1 were generated by well-known PCR methods as described in Yolov and Shabarova (1990) and standard cloning techniques as described in Green & Sambrook (eds), Molecular Cloning, 4th edition, CSHL were used. Combinatorial libraries were screened for optimized variants as described in example 3.

EXAMPLE 6

Figure 3:
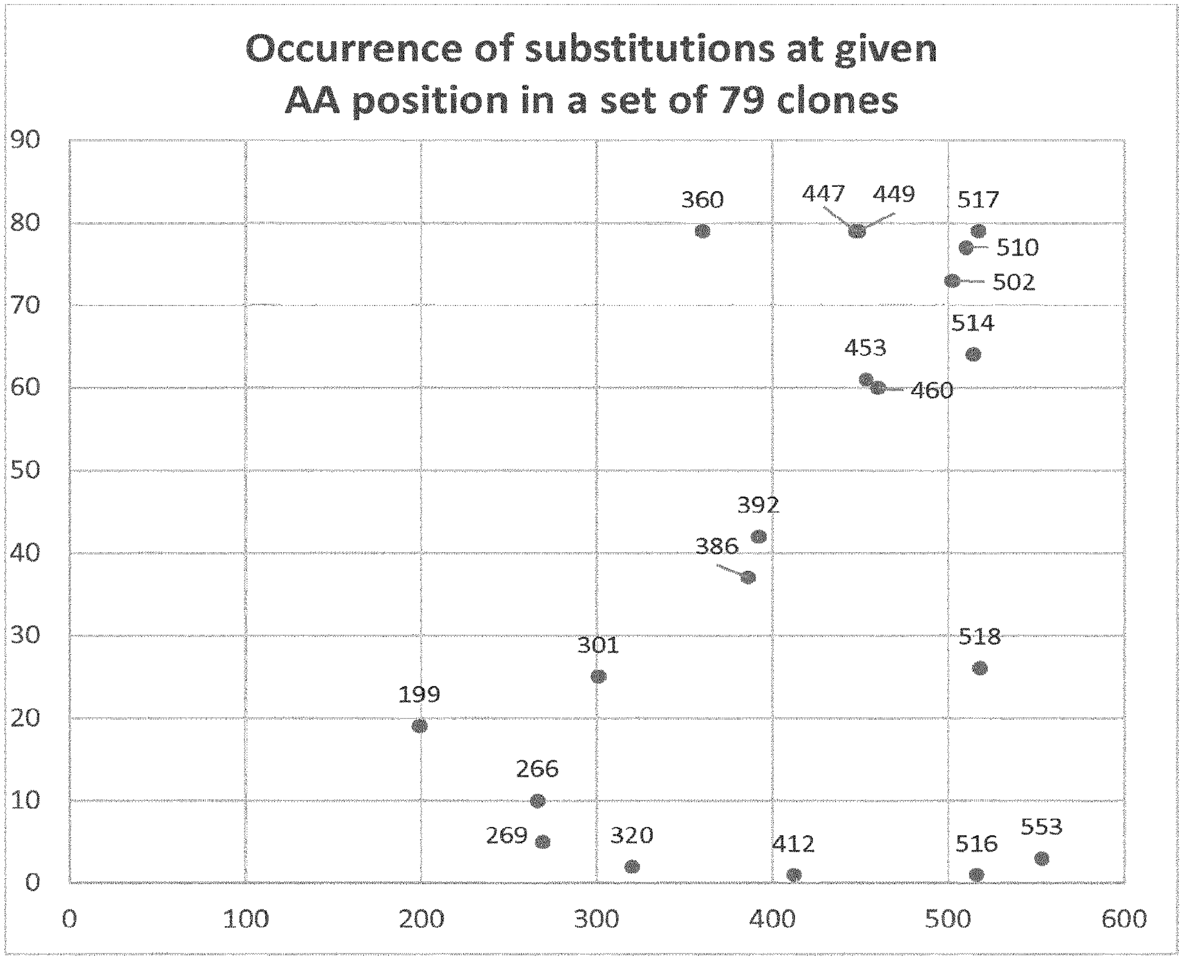
FIGS. 3-5 show the occurrence of substitutions at AA position in different sets of distinct clones and combinatorial clones.

Distinct clones and combinatorial clones comprising two or more mutations from Table 1 were identified, the IT50 analyzed as described above and compared to the IT50 of the used backbone (=wildtype with missing N-terminal methionine) characterizing the variant by the corresponding ΔIT50. As the IT50 of the backbone was determined in the same experiment as the variant the measured IT50 of the backbone can be slightly different from the average value. Results are shown in the following Table 2a (FIG. 3 shows results in graphic form):

TABLE 2a

| Distinct clones comprising selected combinations of mutations from table 1, and their ΔIT 50 compared to the wildtype | | | | | | | |
|---|---|---|---|---|---|---|---|
| # | Mutations in distinct clones and selected combinatorial clones | | | | | | |
| 1 | | | | | E360L | | A392V |
| 2 | | | T301S | | E360V | A3861 | |
| 3 | | | | | E360L | A3861 | A392V |
| 4 | | | | | E360L | | A3921 |
| 5 | | | | | E360V | A3861 | A3921 |
| 6 | | | T301S | G320A | E360L | | |
| 7 | | | T301S | | E360L | A3861 | A3921 |
| 8 | | | T301S | | E360V | | A3921 |
| 9 | | | | | E360V | | A392V |
| 10 | | | | | E360L | A3861 | |
| 11 | | | T301S | | E360L | | A3921 |
| 12 | | | T301S | | E360L | A3861 | |
| 13 | | | | | E360L | A3861 | A3921 |
| 14 | | | | | E360V | | A392V |
| 15 | | | | | E360L | A3861 | |
| 16 | | | T301S | | E360L | | |
| 17 | | | T301S | | E360L | | A392V |
| 18 | | | T301S | | E360V | A3861 | |
| 19 | | | | | E360V | A3861 | |
| 20 | | | T301S | | E360V | | A3921 |
| 21 | D199E | | | | E360V | | |
| 22 | | | | | E360L | A3861 | |
| 23 | | | | | E360L | A3861 | A3921 |
| 24 | | | | | E360V | | A392V |
| 25 | | E269T | | | E360V | A3861 | |
| 26 | | | T301S | | E360L | | A392V |
| 27 | | | | | E360L | | A392V |
| 28 | | | | | E360V | | A3921 |
| 29 | | | T301S | | E360L | | |
| 30 | | | | | E360L | A3861 | A3921 |

TABLE 2a-continued

Distinct clones comprising selected combinations of mutations from table 1, and their ΔIT 50 compared to the wildtype

| | | | | | | | |
|---|---|---|---|---|---|---|---|
| 31 | | | T301S | | E360L | A3861 | A392V |
| 32 | | | | | E360V | | A3921 |
| 33 | | | T301S | | E360L | | A3921 |
| 34 | | | | | E360V | | |
| 35 | | | | | E360L | A3861 | A392V |
| 36 | | | T301S | | E360V | A3861 | |
| 37 | | | | | E360L | A3861 | |
| 38 | | | T301S | | E360L | A3861 | A392V |
| 39 | | | T301S | | E360V | | A392V |
| 40 | | | T301S | | E360L | A3861 | A392V |
| 1 | D447S | A449Y | | A460W | V502C | N510H | |
| 2 | D447S | A449Y | E453W | A460W | V502C | N510H | |
| 3 | D447S | A449Y | E453W | A460W | V502C | N510H | |
| 4 | D447S | A449Y | | A460W | V502C | N510H | |
| 5 | D447S | A449Y | E453W | A460W | V502C | N510H | |
| 6 | D447S | A449Y | E453W | A460W | V502C | N510H | |
| 7 | D447S | A449Y | E453W | | V502C | N510H | |
| 8 | D447S | A449Y | E453W | A460W | V502C | N510H | |
| 9 | D447S | A449Y | E453W | A460W | | N510H | |
| 10 | D447S | A449Y | E453W | A460W | V502C | N510H | |
| 11 | D447S | A449Y | E453W | A460W | V502C | N510H | |
| 12 | D447S | A449Y | E453W | A460W | V502C | N510H | |
| 13 | D447S | A449Y | E453W | A460W | V502C | N510H | |
| 14 | D447S | A449Y | | A460W | V502C | N510H | |
| 15 | D447S | A449Y | E453W | A460W | V502C | N510H | |
| 16 | D447S | A449Y | | A460W | V502C | N510H | |
| 17 | D447S | A449Y | E453W | A460W | V502C | N510H | |
| 18 | D447S | A449Y | E453W | A460W | V502C | N510H | |
| 19 | D447S | A449Y | E453W | A460W | V502C | N510H | |
| 20 | D447S | A449Y | E453W | A460W | V502C | N510H | |
| 21 | D447S | A449Y | | A460W | V502C | N510H | |
| 22 | D447S | A449Y | | A460W | V502C | N510H | |
| 23 | D447S | A449Y | E453W | A460W | V502C | N510H | |
| 24 | D447S | A449Y | E453W | A460W | V502C | N510H | |
| 25 | D447S | A449Y | | | V502C | N510H | |
| 26 | D447S | A449Y | E453W | A460W | V502C | N510H | |
| 27 | D447S | A449Y | E453W | A460W | V502C | N510H | |
| 28 | D447S | A449Y | | A460W | V502C | N510H | |
| 29 | D447S | A449Y | E453W | A460W | V502C | N510H | |
| 30 | D447S | A449Y | E453W | A460W | V502C | N510H | |
| 31 | D447S | A449Y | E453W | A460W | V502C | N510H | |
| 32 | D447S | A449Y | E453W | A460W | V502C | N510H | |
| 33 | D447S | A449Y | E453W | A460W | V502C | N510H | |
| 34 | D447S | A449Y | E453W | A460W | V502C | N510H | |
| 35 | D447S | A449Y | E453W | | V502C | N510H | |
| 36 | D447S | A449Y | E453W | A460W | V502C | N510H | |
| 37 | D447S | A449Y | E453W | A460W | V502C | N510H | |
| 38 | D447S | A449Y | E453W | A460W | V502C | N510H | |
| 39 | D447S | A449Y | E453W | A460W | V502C | N510H | |
| 40 | D447S | A449Y | E453W | A460W | V502C | N510H | |

| # | Mutations in distinct clones and selected combinatorial clones | | IT50 Zymogen | ΔIT 50 Zymogen | IT50 active enzyme | ΔIT 50 active enzyme |
|---|---|---|---|---|---|---|
| 1 | A517T | | 95.5 | 17.0 | 90.1 | 30.6 |
| 2 | A517T | | >95 | >17 | 90.1 | 30.6 |
| 3 | A517T | | 99.5 | 21.0 | 89.2 | 29.7 |
| 4 | A517T | | 97.3 | 18.8 | 89.1 | 29.6 |
| 5 | A517T | | 99.4 | 20.9 | 88.8 | 29.3 |
| 6 | A517T | | 96.4 | 17.9 | 88.6 | 29.1 |
| 7 | A517T | | 96.4 | 17.9 | 88.5 | 29.0 |
| 8 | A517T | | 99.1 | 20.6 | 88.5 | 29.0 |
| 9 | A517T | Q518G | 97.8 | 19.3 | 88.5 | 29.0 |
| 10 | A517T | | 98.4 | 19.9 | 88.4 | 28.9 |
| 11 | A517T | | 97.7 | 19.2 | 88.4 | 28.9 |
| 12 | A517T | | 98.6 | 20.1 | 88.3 | 28.8 |
| 13 | A517T | | 99.5 | 21.0 | 88.2 | 28.7 |
| 14 | A517T | | >95 | >17 | 88.2 | 28.7 |
| 15 | A517T | | 98.3 | 19.8 | 88.1 | 28.6 |
| 16 | A517T | | 95.8 | 17.3 | 88.0 | 28.5 |
| 17 | A517T | | 97.2 | 18.7 | 88.0 | 28.5 |
| 18 | A517T | | 97.6 | 19.1 | 87.8 | 28.3 |
| 19 | A517T | | 98.5 | 20.0 | 87.8 | 28.3 |
| 20 | A517T | Q518G | 97.0 | 18.5 | 87.8 | 28.3 |
| 21 | A517T | | >95 | >17 | 87.8 | 28.3 |
| 22 | A517T | | >95 | >17 | 87.8 | 28.3 |
| 23 | A517T | | 97.1 | 18.6 | 87.8 | 28.3 |

TABLE 2a-continued

| Distinct clones comprising selected combinations of mutations from table 1, and their ΔIT 50 compared to the wildtype | | | | | | |
|---|---|---|---|---|---|---|
| 24 | A517T | | 99.0 | 20.5 | 87.8 | 28.3 |
| 25 | A517T | | 94.0 | 16.0 | 87.7 | 27.0 |
| 26 | A517T | | 97.4 | 18.9 | 87.7 | 28.2 |
| 27 | A517T | Q518G | 98.0 | 19.5 | 87.7 | 28.2 |
| 28 | A517T | | >95 | >17 | 87.6 | 28.1 |
| 29 | A517T | | 96.5 | 18.0 | 87.6 | 28.1 |
| 30 | A517T | | 99.0 | 20.2 | 87.5 | 28.0 |
| 31 | A517T | | 98.1 | 19.6 | 87.5 | 28.0 |
| 32 | A517T | Q518G | 97.9 | 19.4 | 87.4 | 27.9 |
| 33 | A517T | Q518G | 97.1 | 18.6 | 87.4 | 27.9 |
| 34 | A517T | | 95.6 | 17.1 | 87.4 | 27.9 |
| 35 | A517T | | 98.2 | 19.7 | 87.4 | 27.9 |
| 36 | A517T | | 98.5 | 20.0 | 87.4 | 27.9 |
| 37 | A517T | Q518G | 97.9 | 19.4 | 87.4 | 27.9 |
| 38 | A517T | | >95 | >17 | 87.3 | 27.8 |
| 39 | A517T | | 96.2 | 17.7 | 87.2 | 27.7 |
| 40 | A517T | Q518G | >95 | >17 | 87.1 | 27.6 |

| # | Mutations indistinct clones and selected combinatorial clones | | | | | | | |
|---|---|---|---|---|---|---|---|---|
| 41 | | | | T301S | | E360L | A386I | |
| 42 | | | | | | E360V | | A392I |
| 43 | | | | | | E360V | A386I | A392I |
| 44 | | | | | | E360L | | A392V |
| 45 | D199E | | | | | E360V | | |
| 46 | | | | T301S | | E360L | A386I | A392I |
| 47 | D199E | G266A | | | | E360V | | A392V |
| 48 | | G266A | | | | E360V | | A392V |
| 49 | | | | | | E360L | | A392I |
| 50 | | | | T301S | | E360V | A386I | |
| 51 | | | | | | E360L | A386I | |
| 52 | | | | | | E360L | A386I | |
| 53 | D199E | G266A | | | | E360V | | A392V |
| 54 | | | | | | E360V | A386I | A392I |
| 55 | D199E | G266A | E269H | | | E360V | | A392L |
| 56 | | | | | | E360V | A386I | |
| 57 | | | | | | E360V | | A392V |
| 58 | | | | T301S | | E360L | A386I | A392I |
| 59 | D199E | | | | | E360V | A386I | |
| 60 | | | | | | E360V | A386I | A392I |
| 61 | D199E | | | | | E360V | A386I | |
| 62 | | | | | | E360V | A386I | |
| 63 | D199E | G266A | | T301S | | E360L | | |
| 64 | D199E | G266A | E269T | | G320A | E360V | | A392L |
| 65 | | | | | | E360L | A386I | |
| 66 | | G266A | | | | E360V | | A392V |
| 67 | | | | | | E360L | A386I | |
| 68 | D199E | | | | | E360V | | |
| 69 | D199E | | | | | E360V | A386I | |
| 70 | D199E | | | | | E360L | | |
| 71 | D199E | G266A | E269H | T301S | | E360L | | |
| 72 | D199E | | | | | E360L | | |
| 73 | D199E | G266A | | | | E360V | | |
| 74 | D199E | G266A | E269H | | | E360V | | A392L |
| 75 | D199E | | | | | E360V | | |
| 76 | | | | T301S | | E360L | | A392I |
| 77 | D199E | | | | | E360V | | |
| 78 | D199E | | | | | E360L | | |
| 79 | | | | | | E360V | A386I | |
| 41 | | D447S | A449Y | E453W | A460W | V502C | N510H | |
| 42 | | D447S | A449Y | | A460W | | N510H | |
| 43 | | D447S | A449Y | E453W | | V502C | N510H | |
| 44 | | D447S | A449Y | E453W | A460W | | N510H | |
| 45 | | D447S | A449Y | E453W | A460W | V502C | N510H | |
| 46 | | D447S | A449Y | E453W | A460W | V502C | N510H | |
| 47 | | D447S | A449Y | E453W | A460W | V502C | N510H | |
| 48 | R412E | D447S | A449Y | E453W | A460W | | | |
| 49 | | D447S | A449Y | E453W | | V502C | N510H | |
| 50 | | D447S | A449Y | | A460W | V502C | N510H | |
| 51 | | D447S | A449Y | E453W | | V502C | N510H | |
| 52 | | D447S | A449Y | | A460W | V502C | N510H | |
| 53 | | D447S | A449Y | E453W | A460W | V502C | N510H | |
| 54 | | D447S | A449Y | E453W | A460W | V502C | N510H | |
| 55 | | D447S | A449Y | E453W | A460W | V502C | N510H | |
| 56 | | D447S | A449Y | E453W | | V502C | N510H | |
| 57 | | D447S | A449Y | E453W | A460W | V502C | N510H | |
| 58 | | D447S | A449Y | | A460W | V502C | N510H | |

TABLE 2a-continued

| Distinct clones comprising selected combinations of mutations from table 1, and their ΔIT 50 compared to the wildtype | | | | | | |
|---|---|---|---|---|---|---|
| 59 | D447S | A449Y | | | V502C | N510H |
| 60 | D447S | A449Y | E453W | A460W | V502C | N510H |
| 61 | D447S | A449Y | E453W | | V502C | N510H |
| 62 | D447S | A449Y | | A460W | V502C | N510H |
| 63 | D447S | A449Y | E453W | | V502C | N510H |
| 64 | D447S | A449Y | E453W | A460W | V502C | N510H |
| 65 | D447S | A449Y | | | V502C | N510H |
| 66 | D447S | A449Y | E453W | A460W | | |
| 67 | D447S | A449Y | E453W | | V502C | N510H |
| 68 | D447S | A449Y | E453W | | V502C | N510H |
| 69 | D447S | A449Y | E453W | A460W | V502C | N510H |
| 70 | D447S | A449Y | | A460W | V502C | N510H |
| 71 | D447S | A449Y | E453W | | V502C | N510H |
| 72 | D447S | A449Y | E453W | | V502C | N510H |
| 73 | D447S | A449Y | E453W | | V502C | N510H |
| 74 | D447S | A449Y | E453W | A460W | V502C | N510H |
| 75 | D447S | A449Y | | A460W | V502C | N510H |
| 76 | D447S | A449Y | E453W | A460W | | N510H |
| 77 | D447S | A449Y | E453W | | V502C | N510H |
| 78 | D447S | A449Y | E453W | | V502C | N510H |
| 79 | D447S | A449Y | | | V502C | N510H |

| # | Mutations in distinct clones and selected combinatorial clones | | | | IT50 Zymogen | ΔIT 50 Zymogen | IT50 active enzyme | ΔIT 50 active enzyme |
|---|---|---|---|---|---|---|---|---|
| 41 | | A517T | Q518G | | 98.4 | 19.9 | 87.0 | 27.5 |
| 42 | | A517T | | | 92.7 | 14.2 | 86.9 | 27.4 |
| 43 | | A517T | | | >95 | >17 | 86.9 | 27.4 |
| 44 | | A517T | | | 96.9 | 18.4 | 86.8 | 27.3 |
| 45 | | A517T | | | 93.5 | 15.1 | 86.7 | 26.0 |
| 46 | | A517T | Q518G | | 97.4 | 18.9 | 86.7 | 27.2 |
| 47 | | A517T | Q518G | | 101.5 | 23.0 | 86.6 | 27.1 |
| 48 | | A517T | Q518G | | 100.3 | 21.8 | 86.6 | 27.1 |
| 49 | | A517T | Q518G | | >95 | >17 | 86.6 | 27.1 |
| 50 | | A517T | Q518G | | 94.7 | 16.2 | 86.5 | 27.0 |
| 51 | | A517T | | | >95 | >17 | 86.5 | 27.0 |
| 52 | | A517T | | | >95 | >17 | 86.4 | 26.9 |
| 53 | | A517T | Q518G | P553K | 102.2 | 23.7 | 86.4 | 26.9 |
| 54 | | A517T | Q518G | | >95 | >17 | 86.4 | 26.9 |
| 55 | | A517T | Q518G | P553K | 101.7 | 23.2 | 86.3 | 26.8 |
| 56 | | A517T | | | 93.1 | 14.6 | 86.2 | 27.0 |
| 57 | | A517T | Q518G | | >95 | >17 | 86.2 | 26.7 |
| 58 | | A517T | Q518G | | >95 | >17 | 86.2 | 26.7 |
| 59 | | A517T | | | 92.2 | 14.1 | 86.1 | 25.4 |
| 60 | | A517T | Q518G | | 97.2 | 18.7 | 86.0 | 26.5 |
| 61 | | A517T | | | 93.2 | 14.9 | 85.9 | 26.2 |
| 62 | | A517T | | | 92.4 | 13.9 | 85.9 | 26.6 |
| 63 | | A517T | | | 95.7 | 17.2 | 85.8 | 26.3 |
| 64 | | A517T | Q518G | P553K | 100.1 | 21.6 | 85.8 | 26.8 |
| 65 | | A517T | | | 94.0 | 15.9 | 85.8 | 25.1 |
| 66 | R516I | A517T | Q518G | | 100.1 | 21.6 | 85.7 | 26.2 |
| 67 | | A517T | | | >95 | >17 | 85.7 | 26.2 |
| 68 | | A517T | Q518G | | >95 | >17 | 85.7 | 26.2 |
| 69 | | A517T | | | 94.9 | 16.6 | 85.4 | 25.7 |
| 70 | | A517T | | | −10.0 | −10.0 | 85.4 | 25.9 |
| 71 | | A517T | | | 95.8 | 17.3 | 85.4 | 25.9 |
| 72 | | A517T | Q518G | | >95 | >17 | 85.4 | 25.9 |
| 73 | | A517T | Q518G | | >95 | >17 | 85.4 | 25.9 |
| 74 | | A517T | Q518G | | 100.4 | 21.9 | 85.3 | 25.8 |
| 75 | | A517T | | | >95 | >17 | 85.3 | 25.8 |
| 76 | | A517T | Q518G | | 95.1 | 16.6 | 85.2 | 25.7 |
| 77 | | A517T | | | 94.9 | 16.4 | 85.1 | 25.5 |
| 78 | | A517T | | | >95 | >17 | 85.1 | 25.6 |
| 79 | | A517T | | | 93.0 | 15.0 | 85.0 | 25.7 |

It is important to understand that the resulting ΔIT50 of the distinct clones of Tables 2a, 2 b and 4 does not necessarily represent the arithmetic sum of the ΔIT50 of the individual mutations comprised in the distinct clones, as e.g. shown in Table 6.

It is further important to understand that some mutations do have different effects in the zymogen compared to the activated enzyme, as can be seen from the combinatorial clones having the highest stabilizing effect for the zymogen as shown in Tables 2a and 2b.

Figure 4:
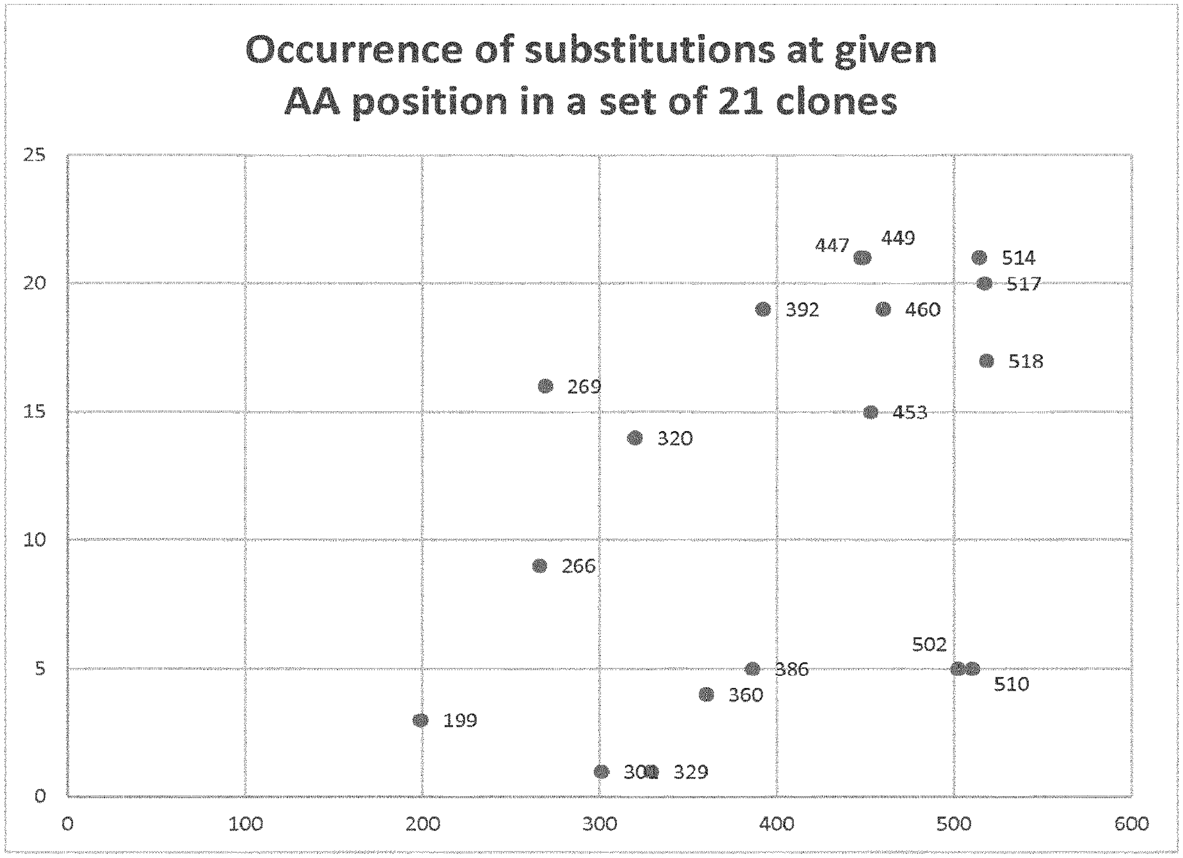

Table 2b shows clones and mutations based on the IT50 of the zymogen which are not shown in Table 2a. (FIG. 4 shows results in graphic form):

TABLE 2b

Distinct clones comprising selected combinations of mutations from Table 1, ranked by the IT50 of the zymogen and their IT50 compared to the wildtype

| # | mutations in distinct clones and selected combinatorial clones | | | | | | | | | | |
|---|---|---|---|---|---|---|---|---|---|---|---|
| 1 | D199E | | | | | | E360V | | A392V | D447S | A449Y |
| 2 | D199E | | | | | | E360L | | A392V | D447S | A449Y |
| 3 | | T301S | | | | | E360L | A386I | | D447S | A449Y |
| 4 | D199E | | G266A | | | | | | A392V | D447S | A449Y |
| 5 | | | G266A | E269T | | | | | A392L | D447S | A449Y |
| 6 | | | G266A | | G320A | | E360L | | A392V | D447S | A449Y |
| 7 | | | G266A | E269T | | | | A386I | A392L | D447S | A449Y |
| 8 | | | G266A | E269T | G320A | | | | A392L | D447S | A449Y |
| 9 | | | | E269H | | | | A386I | A392V | D447S | A449Y |
| 10 | | | | E269H | G320A | | | | A392L | D447C | A449Y |
| 11 | | | G266A | E269Q | G320A | | | | A392L | D447S | A449M |
| 12 | | | | E269H | G320A | | | | A392L | D447S | A449M |
| 13 | | | | E269T | G320A | | | | A392V | D447S | A449Y |
| 14 | | | | E269H | G320A | | | | A392V | D447S | A449Y |
| 15 | | | | E269H | G320A | | | A386I | A392L | D447S | A449M |
| 16 | | | G266A | E269Q | G320A | | | | A392L | D447S | A449M |
| 17 | | | | E269H | G320A | | | | | D447S | A449Y |
| 18 | | | | E269H | 3320A | | | | A392V | D447S | A449Y |
| 19 | | | G266A | E269T | G320A | | | | A392L | D447S | A449Y |
| 20 | | | | E269H | G320A | | | | A392L | D447S | A449Y |
| 21 | | | G266A | E269H | G320A | A329Q | | A386I | A392V | D447C | A449M |

| # | mutations in distinct clones and selected combinatorial clones | | | | | | | | total substitutions | IT50 Zymogen | IT50 activated Enzyme |
|---|---|---|---|---|---|---|---|---|---|---|---|
| 1 | E453W | | V502C | N510H | A514Y | A517T | Q518G | P553K | 12 | 100.3 | 84.42 |
| 2 | E453W | | V502C | N510H | A514Y | A517T | Q518G | P553K | 12 | 96.36 | 84.31 |
| 3 | E453W | A460W | V502C | N510H | A514T | A517T | | | 11 | 96.61 | 83.73 |
| 4 | E453W | A460W | V502C | N510H | A514Y | A517T | Q518G | | 12 | 97.99 | 82.38 |
| 5 | E453W | A460W | V502C | N510H | A514Y | A517T | Q518G | | 12 | 97.41 | 81.03 |
| 6 | E453W | A460W | | | A514Y | A517T | Q518G | | 11 | 96.27 | 80.3 |
| 7 | | A460W | | | A514Y | A517T | Q518G | | 10 | 95.99 | 74.55 |
| 8 | E453W | A460W | | | A514Y | A517T | Q518G | | 11 | 99.78 | 74.16 |
| 9 | | A460W | | | A514Y | A517T | Q518G | | 9 | 95.86 | 73.37 |
| 10 | E453W | A460W | | | A514Y | A517T | Q518G | | 10 | 96.55 | 72.94 |
| 11 | | A460W | | | A514Y | A517T | Q518G | | 10 | 96.01 | 72.85 |
| 12 | E453W | A460W | | | A514Y | A5171 | Q518G | | 10 | 98.41 | 72.8 |
| 13 | E453W | A460W | | | A514Y | A517T | | | 9 | 96.45 | 72.74 |
| 14 | E453W | A460W | | | A514Y | A517T | Q518G | | 10 | 97.95 | 72.32 |
| 15 | | A460W | | | A514Y | A517T | Q518G | | 10 | 98.3 | 72.22 |
| 16 | | A460W | | | A514Y | A517T | Q518G | | 10 | 96.1 | 72.2 |
| 17 | E453W | A460W | | | A514Y | A517T | Q518G | | 9 | 96.57 | 71.84 |
| 18 | | A460W | | | A514Y | A517T | Q518G | | 9 | 96.01 | 71.51 |
| 19 | E453W | A460W | | | A514Y | A517T | | | 10 | 96.02 | 71.22 |
| 20 | E453W | A460W | | | A514Y | A517T | | | 9 | 95.88 | 69.68 |
| 21 | E453W | A460W | | | A514Y | | Q518G | | 12 | 96 | 69.08 |

The finding that in some mutations the stabilizing effect is reduced in the activated enzyme compared to the zymogen, can be explained, without bound to theory, by proximity to the propeptide and potentially optimized interactions between propeptide and enzyme core.

It is thus dependent on the application or storage conditions to decide whether mutations are combined that have the highest effect in stabilizing the zymogen or the active enzyme.

Applications with lower pH before thermal treatments, i.e., premixes with extremely low pH, can dictate to use a variant enzyme with a combination of single mutations stabilizing the activated enzyme most, whereas conditions with higher pH before thermal treatment allow to combine mutations stabilizing the zymogen more than the activated enzyme and thereby also making use of the thermal stabilizing effect of the propeptide which in this case is additive to the effect of the mutations.

It might furthermore make sense to combine mutations that stabilize both enzyme forms equally well, i.e., the zymogen and the activated enzyme, though not having the highest absolute stabilizing effect.

In the following Table 3 and FIG. 1, some preferred substitutions are shown. A preferred protease variant has at least one of these amino acid substitutions compared to the Kumamolisin AS as set forth in SEQ ID NO 1 or 4. The reason for these substitutions to be preferred is either that a) as solitary substitutions, they confer a particular ΔIT50 (zymogen or activated enzyme), or b) they do occur frequently in preferred combinatorial and distinct variants.

TABLE 3

Some preferred substitutions and their key characteristics

| Position | Mutation | ΔIT50 Zymogen | ΔIT50 activated Enzyme | Frequency of occurence in Top combinatorial and distinct variants: activated enzyme (IT50 >80° C.) (total variants measured: 146) | Frequency of occurence in Top combinatorial and distinct variants: zymogen (IT50 >85° C.) (total variants measured: 554) |
|---|---|---|---|---|---|
| D447 | S | 4.0 | 3.2 | 138 | 331 |
| | C | 3.0 | 1.4 | | 33 |
| | A | 1.6 | 1.3 | | |
| A449 | Y | 1.7 | 0.7 | 138 | 303 |
| | N | 1.6 | 3.3 | | |
| | E | 1.6 | 0.4 | | 7 |
| | L | 0.8 | 0.3 | | |
| | M | 1.9 | −0.9 | | 42 |
| A517 | T | 1.3 | 3.9 | 138 | 176 |
| | S | 0.3 | 7.7 | | 79 |
| N510 | H | 2.4 | 7.9 | 125 | 175 |
| V502 | C | 2.3 | 1.9 | 118 | 164 |
| E453 | W | 2.4 | 0.0 | 106 | 295 |
| | Y | 2.6 | 0.7 | | 33 |
| | F | 1.1 | −0.5 | | |
| E360 | L | 1.4 | 3.1 | 62 | 118 |
| | V | 2.4 | 2.9 | 74 | 93 |
| | C | 2.3 | 2.3 | | 49 |
| A514 | T | 2.2 | 1.3 | 11 | 52 |
| | Y | 1.3 | −1.2 | 87 | 217 |
| | D | 1.5 | 1.2 | | |
| | S | 2.4 | 0.5 | | |
| A460 | W | 2.6 | 0.5 | 85 | 300 |
| | R | 2.0 | −0.6 | | 15 |
| A392 | V | 2.8 | 0.7 | 38 | 133 |
| | L | 3.0 | 0.9 | 4 | 75 |
| | I | 3.7 | 2.4 | 22 | 18 |
| | M | 2.3 | 2.0 | | |
| A386 | I | 3.6 | 0.5 | 55 | 164 |
| | L | 2.7 | 1.3 | | 1 |
| | V | 2.1 | 1.2 | | 4 |
| | M | 1.7 | 0.0 | | |
| T301 | S | 0.6 | 7.6 | 43 | 2 |
| | C | 0.8 | 1.0 | 1 | 5 |
| | M | 0.7 | 0.5 | | |
| D199 | E | 0.5 | 1.0 | 43 | 30 |
| Q518 | G | 1.6 | 4.1 | 36 | 250 |
| G266 | A | 1.7 | 0.0 | 33 | 152 |
| P553 | K | 0.5 | 0.3 | 20 | 6 |
| E269 | M | 2.4 | −0.1 | | |
| | T | 2.6 | −0.1 | 5 | 84 |
| | C | 2.1 | −1.2 | | 2 |
| | H | 4.0 | −0.5 | 6 | 180 |
| | Q | 2.0 | −1.4 | | 10 |
| R412 | Q | 0.5 | 2.4 | 1 | 0 |
| | M | 1.5 | 2.9 | 1 | 1 |
| | E | 1.8 | 4.4 | 1 | 1 |
| | D | 0.4 | 3.5 | 1 | 1 |
| S435 | I | 1.7 | 1.6 | 1 | 3 |
| | R | 1.8 | 0.5 | | 9 |
| | T | 2.5 | 4.7 | 1 | 1 |
| | V | 1.6 | 2.1 | 1 | 1 |
| G320 | A | 3.0 | −0.2 | 2 | 186 |
| | Q | 3.6 | 1.5 | | 46 |
| | S | 1.0 | 0.6 | | 35 |
| T326 | R | 1.7 | 1.2 | | 11 |
| | W | 0.9 | 0.2 | | |
| | L | 1.7 | 1.6 | 1 | 6 |
| | K | 1.9 | 1.2 | 1 | 1 |
| T461 | V | 1.2 | 0.0 | 1 | 26 |
| | C | 1.2 | 0.6 | | 48 |
| Q244 | C | 0.5 | −3.6 | | 46 |
| | G | 0.7 | 1.5 | 1 | 1 |
| D293 | Y | 0.8 | 1.0 | 1 | 24 |
| | F | 1.1 | 1.3 | | |
| A487 | Q | 0.0 | 1.6 | 1 | 24 |
| V274 | I | 1.8 | 1.3 | | 104 |
| A372 | S | 2.4 | −0.7 | | 82 |
| K283 | L | 0.6 | −0.2 | | 68 |
| T308 | C | 0.5 | −0.8 | | 30 |

TABLE 3-continued

| Some preferred substitutions and their key characteristics | | | | | |
|---|---|---|---|---|---|
| | | | | Frequency of occurence in Top combinatorial and distinct variants | |
| Position | Mutation | ΔIT50 Zymogen | ΔIT50 activated Enzyme | activated enzyme (IT50 >80° C.) (total variants measured: 146) | zymogen (IT50 >85° C.) (total variants measured: 554) |
| A418 | W | 2.8 | 0.2 | | 12 |
| | H | 1.1 | 1.3 | | 16 |
| i391 | W | 1.7 | 0.6 | | 21 |
| A423 | V | 1.1 | 0.8 | | 18 |
| A331 | F | 2.0 | 0.6 | | 7 |
| | Y | 1.3 | 0.6 | | 9 |
| S327 | F | 1.2 | 0.6 | | |
| | L | 1.5 | 1.1 | | 16 |
| | W | 2.0 | 1.0 | | |
| i219 | L | 1.1 | 0.8 | | 16 |
| M333 | I | 2.5 | −0.7 | | 16 |
| A329 | Q | 2.8 | 0.2 | | 5 |
| | H | 2.1 | 0.3 | | 3 |
| | T | 1.0 | 0.9 | | 7 |
| N515 | G | 2.0 | −0.2 | | 13 |
| A378 | G | 1.5 | 1.5 | | 12 |
| S434 | G | 1.9 | 0.7 | | 12 |
| E421 | R | 1.0 | 0.5 | 1 | 11 |
| A433 | G | 1.4 | 1.9 | | 11 |
| S230 | D | 2.8 | −0.8 | | 9 |
| Q393 | S | 0.9 | 0.2 | | 3 |
| D399 | S | 2.3 | 2.1 | | 4 |
| Y490 | W | 1.5 | 0.3 | | 2 |
| G281 | R | 2.0 | 5.4 | | |
| Y287 | K | 0.2 | 5.2 | | |
| R516 | I | 1.2 | 4.3 | | |
| | E | 1.1 | 3.5 | | |
| | L | 0.5 | 1.2 | | |
| A475 | V | −0.3 | 3.7 | | |
| S354 | E | 1.6 | 3.3 | | |
| S315P | P | 0.8 | 3.0 | | |
| W325 | K | −0.3 | 2.7 | | |
| L442 | W | −0.7 | 2.4 | | |
| | W | 1.4 | 0.3 | | |
| A470 | V | 0.6 | 2.3 | | |
| S324 | R | 0.7 | 2.0 | | |
| S324 | L | 0.1 | 1.3 | | |
| Q361 | C | 0.9 | 1.5 | | |
| Q361 | L | 0.2 | 0.1 | | |
| A190 | D | 1.5 | 0.8 | | |
| T196 | S | 0.7 | 0.3 | | |
| Q202 | D | 0.4 | −0.3 | | |
| E228 | Q | 0.7 | 0.1 | | |
| A229 | W | 0.2 | n.d. | | |
| A242 | S | 0.3 | −0.4 | | |
| D251 | S | 0.8 | −0.4 | | |
| S262 | C | 0.9 | −0.3 | | |
| N291 | T | 0.7 | 0.5 | | |
| N291 | S | −0.2 | 1.0 | | |
| L297 | T | 1.2 | 0.2 | | |
| H305 | F | 0.4 | −0.4 | | |
| H305 | W | 0.1 | −2.7 | | |
| D306 | S | 0.3 | −0.5 | | |
| V314 | M | 0.6 | 0.3 | | |
| V314 | L | 2.5 | 0.7 | | |
| A328 | W | 0.6 | 0.5 | | |
| A328 | D | 1.3 | 1.1 | | |
| A328 | R | 1.1 | 0.1 | | |
| A328 | Y | 1.5 | 0.8 | | |
| I330 | L | 1.1 | 0.8 | | |
| M333 | Y | 0.3 | 1.0 | | |
| M333 | L | 2.4 | −1.0 | | |
| L338 | R | −0.5 | 1.5 | | |
| A342 | R | −0.6 | 3.9 | | |
| A351 | S | 1.3 | −0.9 | | |
| S354 | Q | 2.0 | 0.3 | | |
| D358 | G | −2.0 | 0.7 | | |
| G388 | C | 0.6 | −3.5 | | |
| D402 | E | 0.6 | 1.7 | | |
| V455 | I | 1.2 | 0.3 | | |

TABLE 3-continued

| Some preferred substitutions and their key characteristics | | | | | |
|---|---|---|---|---|---|
| | | | | Frequency of occurence in Top combinatorial and distinct variants | |
| Position | Mutation | ΔIT50 Zymogen | ΔIT50 activated Enzyme | activated enzyme (IT50 >80° C.) (total variants measured: 146) | zymogen (IT50 >85° C.) (total variants measured: 554) |
| V455 | L | 1.8 | 0.7 | | |
| E459 | W | 0.9 | −0.3 | | |
| A478 | L | 1.2 | 0.2 | | |
| K483 | A | 1.5 | 0.7 | | |
| Q497 | Y | 1.8 | 1.2 | | |
| Q497 | M | 0.8 | 0.8 | | |
| Q497 | D | 0.3 | 1.0 | | |
| Q497 | R | 0.6 | 0.2 | | |
| V502 | T | 1.5 | 1.6 | | |
| T507 | L | 0.2 | 1.0 | | |
| L540 | V | 0.7 | 0.5 | | |
| Q542 | H | 0.9 | −0.2 | | |
| Q542 | D | 1.1 | 0.4 | | |
| Q542 | S | 0.4 | 0.5 | | |
| A548 | S | 0.2 | n.d. | | |
| P551 | N | 0.9 | −0.4 | | |
| P551 | R | 0.6 | 0.3 | | |
| P553 | L | 0.8 | 0.2 | | |
| R166 | I | 1.0 | 0.7 | | |
| D265 | T | 1.7 | n.d. | | |

It is further to be understood that the mutations can have positive or negative effects on other enzyme parameters, as the producibility in fermentative microbial production systems or the stability against pH-conditions or endogenous proteases of the animal, like pepsin. Testing the stability of feed enzymes at low pH and in the presence of pepsin is a standard for feed enzymes and was performed in this study as outlined in example 1e. The stability against higher ionic strength is not a standard test for feed enzymes though high ion concentrations can interfere with the enzyme stability and with the enzyme performance under such conditions and can be found for example in the gut. The secretion of acid in the gut and the feed ingredients translate to an increased ionic strength.

Figure 2:
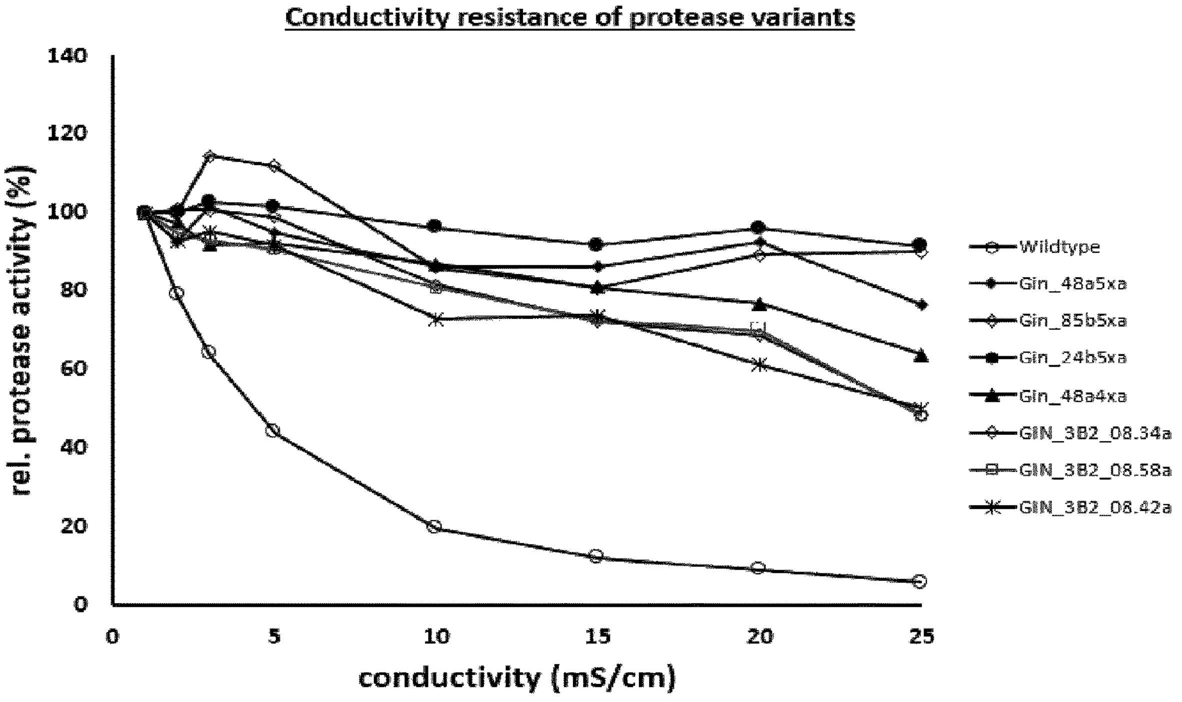
FIG. 2 shows the effects of the ionic strength on stability and performance for the WT and top variants #1 to #7 from table 4.

FIG. 2 shows that the wildtype suffers from combined effects of stability and performance reduction in the presence of higher ionic strength. FIG. 2 also shows the effect of ionic strength on the top variants also shown in table 4, variants #1 to #7.

The performance and stability in high ionic strength was tested as described in example 1d. The pH profile was a control parameter and tested as described in example 1f. The digestion of proteinaceous antinutritive factors like the Trypsin/chymotrypsin inhibitors BBI and KTI (Bowman-Birk inhibitors and Kunitz-type inhibitors) is a potential beneficial performance characteristic of a protease which was tested as described in example 1g.

Figure 5:
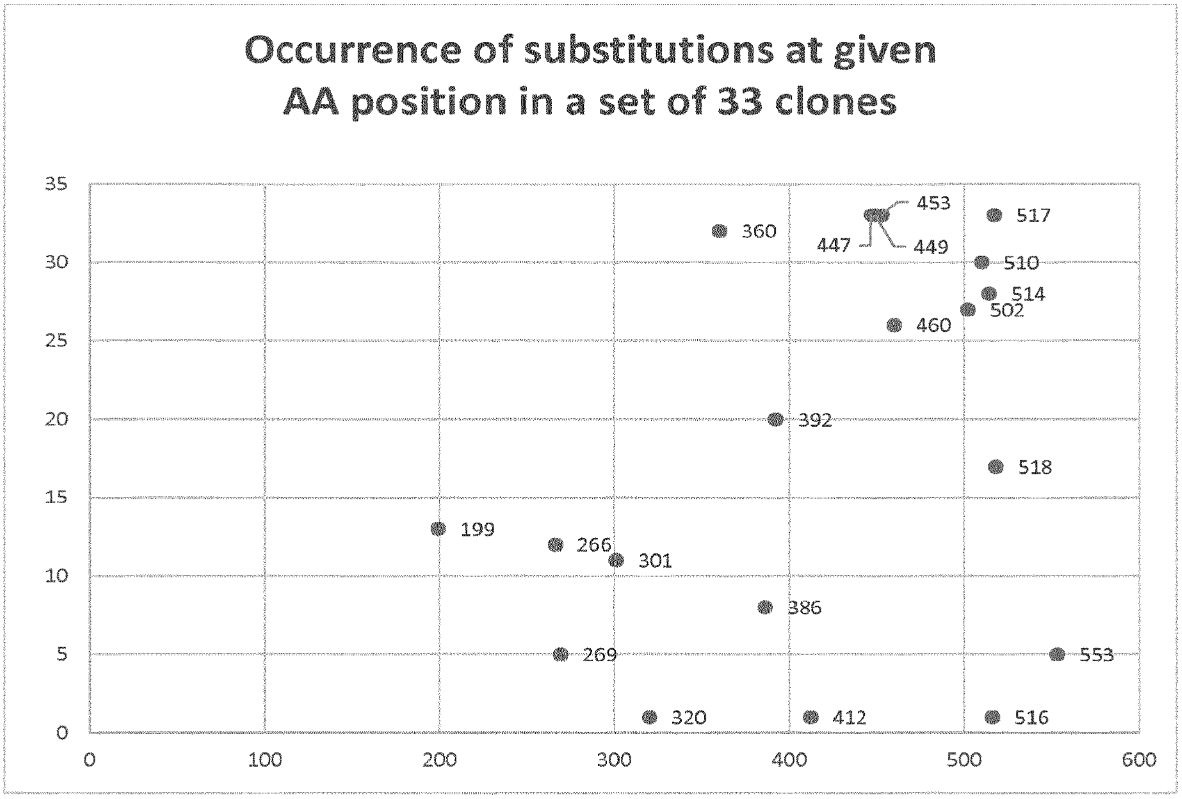

From the 651 individual combinatorial and distinct variants tested in detail, Table 4 describes the variants consolidating a multitude of performance and stability parameters (FIG. 5 shows results in graphic form).

All variants shown in table 4 are better or equally well produced in a microbial production system than the wildtype and have no relevant changes in their pH activity profile tested as described in example 1d. Table 4 ranks these variants based on the thermal stability of the activated enzyme, the pH/pepsin stability and the stability against and the performance under higher ionic strength.

It was further found that the best variants can hydrolyze BBI and KTI (Bowman-Birk inhibitors and Kunitz-type inhibitors) as tested in a functional trypsin inhibition assay, which differentiates these variants from the parent enzyme, beside the high thermal stability engineered into these variants.

TABLE 4

| Some distinct and combinatorial clones with particularly good performance | | | | | | | | | | | | | | |
|---|---|---|---|---|---|---|---|---|---|---|---|---|---|---|
| | mutant code | Mutations in distinct clones and selected combinatorial clones | | | | | | | | | | | | |
| 1 | GIN 382 08.42a | | | | 1301S | | E360V | | A3921 | D447S | A449V | E453W | A460W |
| 2 | Gin 48a 5xa | D199E | G266A | | | | E360V | | A392V | D447S | A4499 | E453W | A460W |
| 3 | Gin 85b 5xa | D199E | G266A | E269H | | | E360V | | A392L | D447S | A4490 | E453W | A460W |
| 4 | Gin24b5ya | D199E | G266A | F2697 | | G320A | E360V | | A392L | D4475 | A449Y | E453W | A460W |
| 5 | GIN 382 08.34a | | | | | | E360V | A3861 | | D447S | A449V | E453W | A460W |
| 6 | GIN 382 08.58a | | | | | | E360L | | A392V | D447S | A449V | E453W | A460W |
| 7 | Gin 48a ha | D199E | G266A | | | | E360V | | A392V | D447S | A449V | E453W | A460W |
| 8 | GIN_48a lxbxe | | G266A | | | | E360V | | A392V | D447S | A449V | E453W | A460W |
| 9 | GIN 382 08.85c | | | | | | E360V | | A392V | D447S | A449V | E453W | A460W |
| 10 | GIN 382 08.47a | | | | | | E360L | A3861 | | D447S | A449V | E453W | A460W |
| 11 | GIN 3133 05.8k | | | | 13015 | | F3601. | | A392V | D4475 | A449Y | E453W | A460W |
| 12 | GIN 382 10.87a | | | | 1301S | | E360V | | A3921 | D447S | A449V | E453W | A460W |

TABLE 4-continued

Some distinct and combinatorial clones with particularly good performance

| | | | | | | | | | | | | | |
|---|---|---|---|---|---|---|---|---|---|---|---|---|---|
| 13 | GIN 3B3 03.04c | | | | | E360L | A3861 | A3921 | | D447S | A449V | E453W | A460W |
| 14 | GIN 383 01.112 | | | | | E360V | | A392V | | D447S | A449V | E453W | A460W |
| 15 | GIN 383 02.55a | | | | | E360V | | A3921 | | D447S | A449V | E453W | A460W |
| 16 | GIN 382 09.09c | | | | | E360L | A3861 | A392V | | D447S | A449V | E453W | |
| 17 | GIN 313305.09c | | | | | E360L | A3861 | | | D447S | A449V | E453W | A460W |
| 18 | GIN 382 09.312 | | | | 13015 | E360L | A386I | | | D447S | A449V | E453W | A460W |
| 19 | GIN 383 01.52a | | | | | E360L | | A392V | | D447S | A449V | E453W | A460W |
| 20 | GIN 48a lxbxd | | G266A | | | E360V | | A392V | R412E | D447S | A449V | E453W | A460W |
| 21 | GIN 3133 01.2Th | | | | 13015 | E360L | A386I | A3921 | | D447S | A449V | E453W | A460W |
| 22 | Gin 28a 5x2xf | D199E | G266A | | T3015 | E360L | | | | D447S | A449V | E453W | |
| 23 | Gin 2h 5x3xa | D199E | G266A | E269H | 13015 | E360L | | | | D447S | A449V | E453W | |
| 24 | Gin 85134xa | D199E | G266A | E269H | | E360V | | A392L | | D447S | A449V | E453W | A460W |
| 25 | Gin 28a 5x1xf | D199E | | | 13015 | E360L | | | | D447S | A449V | E453W | A460W |
| 26 | Gin2h4xa5x | D199E | | | | E360V | | A392V | | D447S | A449V | E453W | |
| 27 | GIN 48a hb KR | | G266A | | | E360V | | A392V | R412D | D447S | A449Y | E453W | A460W |
| 28 | Gin 2h 4h 6x | D199E | | | | E360L | | A392V | | D447S | A449Y | E453W | |
| 29 | Gn 28a 5xlm | 0199E | | | 1301S | E360L | | | | 0447S | A449Y | E453W | |
| 30 | GIN 383 05.206 | | | | | E360L | | A392V | | D447S | A449Y | E453W | A460W |
| 31 | GIN 382 08.8k | | | | 13015 | E360L | A386I | | | D447S | A449Y | E453W | A460W |
| 32 | Gin 2h 5xhd | D199E | G266A | E269T | 1301S | E360L | | | | D447S | A449Y | E453W | |
| 33 | Gin 48a 3xa | D199E | G266A | | | | | A392V | | D447S | A449Y | E453W | A460W |

| Mutations in distinct clones and selected combinatorial clones | | | | | | | | i750 rtl Zymogen | 1750 rti activated | pH/pepsin Stability % residual | Stability/ performance at 25 mS cm−1 | Inhibitor hydrolysis BBI | KTI |
|---|---|---|---|---|---|---|---|---|---|---|---|---|---|
| 1 | V502C | N510H | A514Y | | A517T | | | 9%10 | 88.48 | 93 | 62 | 48% | 41% |
| 2 | V502C | N510H | A5146 | | A517T | Q518G | P553K | 102.15 | 86.37 | 96 | 87 | 58% | 46% |
| 3 | 0502C | N510H | A5140 | | A517T | Q518G | P553K | 101.73 | 86.34 | 92 | 62 | 60% | 47% |
| 4 | V502C | N510H | A514Y | | A517T | Q518G | P553K | 100.13 | 85.82 | 95 | 77 | 68% | 65% |
| 5 | V502C | N510H | A514Y | | A5171 | | | 98.48 | 87.82 | 99 | 68 | 50% | 48% |
| 6 | V502C | N510H | A514Y | | A517T | Q518G | | 98.00 | 87.65 | 91 | 48 | 45% | 40% |
| 7 | V502C | N510H | A514Y | | A517T | Q518G | | 101.45 | 86.59 | 92 | 81 | 58% | 52% |
| 8 | | | A514Y | R5161 | A5171 | Q518G | | 100.10 | 85.73 | 88 | 98 | 75% | 56% |
| 9 | | N510H | A514T | | A517T | Q518G | | 97.78 | 88.46 | 93 | 33 | 41% | 40% |
| 10 | V502C | N510H | A514Y | | A5171 | | | 98.33 | 88.10 | 92 | 38 | poS. | pos. |
| 11 | V502C | N510H | A5141- | | A517T | | | 97.18 | 87.96 | 90 | 32 | pos. | pos. |
| 12 | V502C | N510H | A514Y | | A5171 | | | 96.99 | 87.81 | 81 | 29 | poS. | pos. |
| 13 | V502C | N510H | A514Y | | A517T | | | 97.06 | 87.79 | 68 | 24 | poS. | pos. |
| 14 | V502C | N510H | A514Y | | A517T | | | 99.01 | 87.75 | 102 | 49 | pos. | 40% |
| 15 | V502C | N510H | A514Y | | A517T | Q518G | | 97.88 | 87.42 | 92 | 32 | | |
| 16 | V502C | N510H | A514Y | | A5171 | | | 98.23 | 87.38 | 80 | 18 | poS. | pos. |
| | | | | | | | | | | | | poS. | pos. |
| 17 | V502C | N510H | A514Y | | A517T | Q518G | | 97.85 | 87.35 | 68 | 32 | poS. | pos. |
| 18 | V502C | N510H | A514Y | | A517T | Q518G | | 98.41 | 86.97 | 79 | 29 | poS. | pos. |
| 19 | | N510H | A514Y | | A5171 | | | 96.85 | 86.75 | 61 | 39 | poS. | pos. |
| 20 | | | A514Y | | A517T | Q518G | | 100.30 | 86.59 | 90 | 89 | 58% | 41% |
| 21 | V502C | N510H | A514Y | | A517T | Q518G | | 9a 50 | 86.59 | 94 | 34 | poS. | pos. |
| 22 | V502C | N510H | A514Y | | A5171 | | | 95.73 | 85.83 | 74 | 51 | poS. | pos. |
| 23 | V502C | N510H | A514Y | | A5171 | | | 95.81 | 85.38 | 75 | 34 | poS. | pos. |
| 24 | V502C | N510H | A514Y | | A517T | Q518G | | 100.40 | 85.34 | 89 | 57 | poS. | pos. |
| 25 | V502C | N510H | | | A517T | | | 94.77 | 84.81 | 95 | 35 | 55% | 40% |
| 26 | V502C | N510H | A514Y | | A5171 | Q518G | P553K | 9a 90 | 84.73 | 95 | 52 | 55% | pos. |
| 27 | | | A514Y | | A5171 | Q518G | | 96.46 | 84.30 | 94 | 70 | 50% | pos. |
| 28 | V502C | N510H | A514Y | | A517T | Q518G | P553K | 9%08 | 84.08 | 112 | 33 | 43% | pos. |
| 29 | V502C | N510H | A514Y | | A5171 | | | >97 | 83.84 | n.d. | 32 | poS. | pos. |
| 30 | | N510H | A514Y | | A5171 | | | >97 | 83.75 | 80 | 30 | 54% | 48% |
| 31 | V502C | N510H | A514T | | A5171 | | | 96.61 | 83.73 | 73 | 28 | 46% | 46% |
| 32 | V502C | N510H | | | A517T | | | 94.68 | 83.66 | 81 | 44 | poS. | pos. |
| 33 | V502C | N510H | A514Y | | A5171 | Q518G | | 97.99 | 82.38 | 101 | 42 | 50% | pos. |

The following Table 5 shows the frequency of occurrence of given mutations preferred combinatorial and distinct variants. The frequency of occurrence is a measure for the role and importance of a given mutation.

TABLE 5

Frequency of occurrence of given mutations in preferred combinatorial and distinct variants. Frequency of occurrence is a measure for the role and importance of a given mutation.

| Mutation | Frequency of occurence in preferred combinatorial and distinct variants (activated enzyme (IT50 > 80° C.)) | Mutation | Frequency of occurence in preferred combinatorial and distinct variants zymogen (IT50 > 85° C.) | Mutation | Frequency of occurence in preferred combinatorial and distinct variants zymogen (IT50 > 85° C.) |
|---|---|---|---|---|---|
| D447S | 127 | D447S | 365 | A331F | 7 |
| A449Y | 127 | A449Y | 353 | A331Y | 9 |
| A517T | 127 | A517T | 256 | A329Q/H/T | 15 |
| N510H | 125 | N510H | 175 | S435R/I | 11 |
| E360L/V | 125 | E360L/V | 262 | V274I | 104 |
| V502C | 120 | V502C | 185 | A372S | 82 |
| E453W | 92 | E453W | 320 | K283L | 56 |
| A514Y/T | 84 | A514Y/T | 265 | Q244C | 46 |
| A460W | 72 | A460W | 308 | T380C | 30 |
| A386I | 56 | A386I | 178 | A418W | 28 |
| A392V/I | 50 | A392V/I | 392 | I391W | 21 |
| T301S | 44 | T301S | 79 | A423V | 18 |
| D199E | 43 | D199E | 30 | T326L | 16 |
| Q518G | 36 | Q518G | 250 | I219L | 16 |
| P553K | 20 | P553K | 6 | S327L | 16 |
| E269T/H | 12 | E269T/H | 133 | M333I | 16 |
| G255A | 19 | G266A | 133 | N515G | 13 |
| D293Y | 1 | D293Y | 24 | A378G | 12 |
| G320A | 1 | G320A | 265 | S434G | 12 |
| R412Q | 1 | R412Q | 74 | A433G | 10 |
| E421R | 1 | E421R | 11 | S230D | 9 |
| A487Q | 1 | A487Q | 24 | Q393S | 3 |
| T461V | 1 | T461V | 26 | D399S | 3 |
| | | T461C | 48 | Y490W | 3 |

The following Table 6 shows the impact of single mutations on ΔIT50 of the zymogen or the activated form. Again, the amount of impact of a single mutation on ΔIT50 is a measure for the role and importance of a said mutation.

TABLE 6

Impact of single mutations on ΔIT 50 of the zymogen (left) or the activated form (right). The amount of impact of a single mutation on ΔIT 50 is a measure for the role and importance of a said mutation.

| Mutation | ΔIT50 Zymogen | Mutation | ΔIT50 Zymogen | Mutation | ΔIT50 activated Enzyme | Mutation | ΔIT50 activated Enzyme |
|---|---|---|---|---|---|---|---|
| D447S | 4.8 | L297T | 1.2 | A517S | 7.7 | D358G | 0.7 |
| E269H | 4.0 | S327F | 1.2 | N510H | 7.6 | A331Y | 0.6 |
| A392I | 3.7 | V455I | 1.2 | T301S | 7.6 | S327F | 0.6 |
| G320Q | 3.6 | T461V | 1.2 | G281R | 5.4 | T461C | 0.6 |
| A386I | 3.6 | T461C | 1.2 | Y287K | 5.2 | G320S | 0.6 |
| G320A | 3.0 | A478L | 1.2 | S435T | 4.7 | A386I | 0.5 |
| A392L | 3.0 | R516I | 1.2 | R412E | 4.4 | A460W | 0.5 |
| D447C | 3.0 | I219L | 1.1 | R516I | 4.3 | A514S | 0.5 |
| S230D | 2.8 | D293F | 1.1 | Q518G | 4.1 | S435R | 0.5 |
| A329Q | 2.8 | A328R | 1.1 | A517T | 3.9 | A190D | 0.5 |
| A392V | 2.8 | I330L | 1.1 | A475V | 3.7 | E421R | 0.5 |
| A418W | 2.8 | A423V | 1.1 | R516E | 3.5 | N291T | 0.5 |
| A386L | 2.7 | E453F | 1.1 | R412D | 3.5 | T301M | 0.5 |
| E269T | 2.6 | R516E | 1.1 | A342R | 3.4 | L540V | 0.5 |
| E453Y | 2.6 | Q542D | 1.1 | D447S | 3.3 | A328W | 0.5 |
| A460W | 2.6 | G320S | 1.0 | S354E | 3.3 | Q542S | 0.5 |
| V314L | 2.5 | A329T | 1.0 | A449N | 3.3 | A449E | 0.4 |
| M333I | 2.5 | E421R | 1.0 | E360L | 3.1 | Q542D | 0.4 |
| S435T | 2.5 | R166I | 1.0 | S315PP | 3.0 | A329H | 0.3 |
| E269M | 2.4 | V410I | 1.0 | E360V | 2.9 | S354Q | 0.3 |
| M333L | 2.4 | S262C | 0.9 | R412M | 2.9 | Y490W | 0.3 |
| E360V | 2.4 | T326W | 0.9 | W325K | 2.7 | L442W | 0.3 |
| A372S | 2.4 | Q361C | 0.9 | A392I | 2.4 | V455I | 0.3 |

TABLE 6-continued

Impact of single mutations on ΔIT 50 of the zymogen (left) or the activated form (right). The amount of impact of a single mutation on ΔIT 50 is a measure for the role and importance of a said mutation.

| Mutation | ΔIT50 Zymogen | Mutation | ΔIT50 Zymogen | Mutation | ΔIT50 activated Enzyme | Mutation | ΔIT50 activated Enzyme |
|---|---|---|---|---|---|---|---|
| E453W | 2.4 | Q393S | 0.9 | R412Q | 2.4 | A449L | 0.3 |
| N510H | 2.4 | E459W | 0.9 | L442W | 2.4 | T196S | 0.3 |
| A514S | 2.4 | Q542H | 0.9 | E360C | 2.3 | V314M | 0.3 |
| E360C | 2.3 | P551N | 0.9 | A470V | 2.3 | P551R | 0.3 |
| A392M | 2.3 | D251S | 0.8 | D399S | 2.1 | P553K | 0.3 |
| D399S | 2.3 | D293Y | 0.8 | S435V | 2.1 | A329Q | 0.2 |
| V502C | 2.3 | T301C | 0.8 | A392M | 2.0 | A418W | 0.2 |
| A514T | 2.2 | S315P | 0.8 | V502C | 1.9 | L297T | 0.2 |
| E269C | 2.1 | A449L | 0.8 | A433G | 1.9 | A478L | 0.2 |
| A329H | 2.1 | Q497M | 0.8 | S324R | 1.9 | T326W | 0.2 |
| A331F | 2.1 | P553L | 0.8 | D402E | 1.7 | Q393S | 0.2 |
| A386V | 2.1 | T196S | 0.7 | T326L | 1.6 | P553L | 0.2 |
| E269Q | 2.0 | E228Q | 0.7 | S435I | 1.6 | Q497R | 0.2 |
| G281 | 2.0 | Q244G | 0.7 | V502T | 1.6 | A331F | 0.1 |
| S327W | 2.0 | N291T | 0.7 | A487Q | 1.6 | A328R | 0.1 |
| S354Q | 2.0 | T301M | 0.7 | G320Q | 1.5 | E228Q | 0.1 |
| A460R | 2.0 | L540V | 0.7 | A378G | 1.5 | Q361L | 0.1 |
| N515G | 2.0 | K283L | 0.6 | Q361C | 1.5 | E453W | 0 |
| T326K | 1.9 | T301S | 0.6 | Q244G | 1.5 | G266A | 0 |
| S434G | 1.9 | V314M | 0.6 | L338R | 1.5 | A386M | 0 |
| A449M | 1.9 | S324R | 0.6 | D447C | 1.4 | I391W | 0 |
| V274I | 1.8 | A328W | 0.6 | A386L | 1.3 | T461V | 0 |
| R412E | 1.8 | G388C | 0.6 | A514T | 1.3 | E269T | −o.i |
| S435R | 1.8 | D402E | 0.6 | V274I | 1.3 | E269M | −o.i |
| V455L | 1.8 | A470V | 0.6 | D447A | 1.3 | Q542H | −o.ι |
| Q497Y | 1.8 | Q497R | 0.6 | D293F | 1.3 | G320A | −0.2 |
| G266A | 1.7 | P551R | 0.6 | S324L | 1.3 | N515G | −0.2 |
| T326R | 1.7 | D199E | 0.5 | A386V | 1.2 | K283L | −0.2 |
| T326L | 1.7 | Q244C | 0.5 | T326K | 1.2 | S262C | −0.3 |
| A386M | 1.7 | T308C | 0.5 | Q497Y | 1.2 | E459W | −0.3 |
| I391W | 1.7 | R412Q | 0.5 | T326R | 1.2 | D251S | −0.3 |
| S435I | 1.7 | R516L | 0.5 | A514D | 1.2 | Q202D | −0.3 |
| A449Y | 1.7 | P553K | 0.5 | R516L | 1.2 | P551N | −0.4 |
| D265T | 1.7 | Q202D | 0.4 | S327L | 1.1 | H305F | −0.4 |
| S354E | 1.6 | H305F | 0.4 | A328D | 1.1 | A242S | −0.4 |
| S435V | 1.6 | R412D | 0.4 | S327W | 1.0 | E269H | −0.5 |
| D447A | 1.6 | Q542S | 0.4 | D293Y | 1.0 | E453F | −0.5 |
| A449E | 1.6 | A242S | 0.3 | T301C | 1.0 | D306S | −0.5 |
| A449N | 1.6 | D306S | 0.3 | D199E | 1.0 | A460R | −0.6 |
| Q518G | 1.6 | M333Y | 0.3 | M333Y | 1.0 | M333I | −0.7 |
| A190D | 1.5 | Q497D | 0.3 | Q497D | 1.0 | A372S | −0.7 |
| S327L | 1.5 | A517S | 0.3 | T507L | 1.0 | S230D | −0.8 |
| A328Y | 1.5 | A229W | 0.2 | N291S | 1.0 | T308C | −0.8 |
| A378G | 1.5 | Y287K | 0.2 | A392L | 0.9 | A449M | −0.9 |
| 412M | 1.5 | Q361L | 0.2 | A329T | 0.9 | A351S | −0.9 |
| K483A | 1.5 | T507L | 0.2 | V455L | 0.8 | M333L | −1.0 |
| Y490W | 1.5 | A548S | 0.2 | A328Y | 0.8 | E269C | −1.1 |
| A514D | 1.5 | S324L | 0.1 | I330L | 0.8 | E269Q | −1.4 |
| E360L | 1.4 | A487Q | 0 | A423V | 0.8 | H305W | −2.7 |
| A433G | 1.4 | N291S | −0.2 | Q497M | 0.8 | G388C | −3.5 |
| L442W | 1.4 | W325K | −0.3 | A392V | 0.7 | Q244C | −3.6 |
| A328D | 1.3 | A475V | −0.3 | E453Y | 0.7 | D265T | n.d. |
| A331Y | 1.3 | L338R | −0.5 | V314L | 0.7 | R166I | n.d. |
| A351S | 1.3 | A342R | −0.6 | S434G | 0.7 | V410I | n.d. |
| A514Y | 1.3 | L442W | −0.7 | A449Y | 0.7 | A229W | n.d. |
| A517T | 1.3 | D358G | −2 | K483A | 0.7 | A548S | n.d. |

It is further to be understood that some mutations of Table 1 and Table 6 can interchangeably be used to engineer thermostability in Kumamolisin As. Table 7 shows a set of variants based on variant #1 of Table 7. In the course of engineering the mutations at position 502 and 510 seemed to change the activity at extrem acidic pH, below pH 2.

Excluding mutations at 502 and 510 reduced the thermostability significantly below the targeted temperature stability for the activated enzyme, as for example in Table 7, clone #2 which has a 7.8° C. reduction in thermal stability compared to clone #1. A set of distinct variants were constructed by a rational approach taking advantage of the mutations identified and shown in Tables 1 and 6 to compensate for the effect of 502 and 510. With the exception of D399S substitutions can gradually or fully compensate the effect of mutations at 502 and 510.

TABLE 7

A set of variants based on variant #1

| # | Mutations in distinct clones and selected combinatorial clones | | | | | | | | | |
|---|---|---|---|---|---|---|---|---|---|---|
| 1 | G266A | | | E360V | A392V | | | | | D4475 | A449Y |
| 2 | G266A | | | E360V | A392V | | | | | D4475 | A449Y |
| 3 | G266A | | | E360V | A392V | | R412E, | | | D4475, | A449Y, |
| 4 | G266A | | | E360V | A392V | | R412D | | | D4475 | A449Y |
| 5 | G266A | | | E360V | A392V | | R412Q | | | D447S | A449Y |
| 6 | G266A | | | E36C.S. | A392S. | | | | 54351 | D447S | A449Y |
| 7 | G266A | | | E360V | A392V | | | A 433G | | D447S | A449Y |
| 8 | G266A | | T326L | E360V | A392V | | | | | D4475 | A449Y |
| 9 | G266A | | | E360V | A392V | | R412M | | | D4475 | A449Y |
| 10 | G266A | | | E360V | A392V | | | | 5435T | D4475 | A449Y |
| 11 | G266A | | | E360V | A392V | | | | | D4475 | A449Y |
| 12 | G266A | | T326K | E360V | A392V | | | | | D4475 | A449Y |
| 13 | G266A | | | E360S. | A392S. | | | | | D447S | A449Y |
| 14 | Q244G | G266A | | E360V | A392V | | | | | D447S | A449Y |
| 15 | G266A | | | E360V | A392V | | | | 5435V | D4475 | A449Y |
| 16 | G266A | | | E360V | A392V | D3995 | | | | D4475 | A449Y |

| # | Mutations in distinct clones and selected combinatorial clones | | | | | | | | IT50 [CC] Zymogen | IT50 [CC] activated |
|---|---|---|---|---|---|---|---|---|---|---|
| 1 | E453W | A460W | | V502C | N510H | A514Y | A517T | Q518G | 101.5 | 86.6 |
| 2 | E453W | A460W | | | | A514Y | A517T | Q518G | >95 | |
| 3 | E453W, | A460W, | | | | A514Y, | A517T, | Q518G, | 100.3 | 78.8 |
| 4 | E453W | A460W | | | | A514Y | A517T | Q518G | | |
| 5 | E453W | A460W | | | | A514Y | A517T | Q518G | 96.5 | 86.6 |
| 6 | E453 V! | A460W | | | | A514Y | A517T | Q518G | 97.7 | |
| 7 | V E453W | A460W | | | | A514Y | A517T | Q518G | 97.4 | 84.3 |
| 8 | E453W | A460W | | | | A514Y | A517T | Q518G | 98.1 | |
| 9 | E453W | A460W | | | | A514Y | A517T | Q518G | 98.7 | 81.8 |
| 10 | E453W | A460W | | | | A514Y | A517T | Q518G | 98.3 | |
| 11 | E453W | A460W | A487Q | | | A514Y | A517T | Q518G | 99.2 | 81.4 |
| 12 | E453W | A460W | | | | A514Y | A517T | Q518G | 96.3 | |
| 13 | E453W | A460W | | | | A514Y | A517T | Q518G | 97.2 | 81.3 |
| 14 | E453W | A460W | | | | A514Y | A517T | Q518G | 96.2 | |
| 15 | E453W | A460W | | | | A514Y | A517T | Q518G | 96.3 | 81.1 |
| 16 | E453W | A460W | | | | A514Y | A517T | Q518G | 98.6 | |

REFERENCES

Wlodawer Al, Li M, Gustchina A, Oyama H, Dunn B M, Oda K., Acta Biochim Pol. 2003; 50 (1): 81-102

Terashita, T., Oda, K., Kono, M. & Murao, S., Agric Biol Chem (1981) 45, 1937-1943

Oda, K., Takahashi, S., Ito, M. & Dunn, B. M., Adv Exp Med Biol (1998) 436, 349-353

Packer & Liu, Methods for the directed evolution of proteins. Nature Reviews Genetics 16, 379-394 (2015)

Hsieh & Vaisvila, Protein engineering: single or multiple site-directed mutagenesis. Methods Mol Biol. 2013; 978: 173-86

Cadwell and Joyce, Mutagenic PCR. PCR Methods Appl. 3, 1994, 136-140

Okubo et al, 2006 June; 273 (11): 2563-76.

What is claimed is:

1. A protease variant comprising an amino acid sequence derived from a Kumamolisin AS, as set forth in an amino acid sequence which is at least 90% identical to SEQ ID NO. 1, or a fragment, or shuffled variant thereof maintaining proteolytic activity, which protease variant has one or more amino acid substitutions, wherein at least one amino acid substitution occurs at the residue position of SEQ ID NO: 1 corresponding to D447 of SEQ ID NO: 4, wherein the protease variant has increased thermostability compared to wild type Kumamolisin *Alicyclobacillus sendaiensis* (AS).

2. The protease variant of claim 1, which protease variant demonstrates at least one altered or improved stability compared to (i) the Kumamolisin AS wildtype as set forth in SEQ ID NO: 4, or (ii) the Kumamolisin AS backbone as set forth in any of SEQ ID NOs: 1-3.

3. The protease variant of claim 1, wherein the at least one amino acid substitution occurring at residue position 446 of SEQ ID NO: 1 corresponding to D447 of SEQ ID NO: 4 is a D447S D to S substitution compared to the Kumamolisin AS as set forth in SEQ ID NO 1.

4. The protease variant of claim 1, which protease variant has at least 2 amino acid substitutions compared to the Kumamolisin AS backbone as set forth in SEQ ID NO:1.

5. The protease variant of claim 1, which protease variant has at least one, at least two, at least three, at least four, at least five, or at least six amino acid substitutions selected from the group consisting of D447S, A449Y, A517T, N51OH, E360L, E360V, E360C, V502C, E453W, A514T, A514Y, A514D, A514S, A460W, and A386I.

6. The protease variant of claim 1, which protease variant has a set of substitutions at selected residues in the Kumamolisin AS backbone as set forth in SEQ ID NO:1, which set is at least one of the following a) 360, 447, 449 and 510 b) 447, 449 and 514, and/or c) 447, 449, 453, and 517.

7. The protease variant of claim 1 wherein said improved stability is improved thermostability (IT50) of either an activated Kumamolisin AS, enzyme or a zymogen of Kumamolisin AS.

8. The protease variant of claim 1, which protease variant has an IT50 of between ≥75° C. and ≤105° C.

9. A composition comprising the protease variant or protease of claim 1, which composition has a pH of ≥5.

10. A feed additive, feed ingredient, feed supplement, and/or feedstuff comprising the protease variant of claim 1.

11. A method comprising combining a protease variant of claim 2 with an animal feed, wherein the protease variant of claim 1 improves digestibility of the animal feed.

12. The protease variant of claim 1, further comprising one or more amino acid substitutions at one or more residue positions in SEQ ID NO: 1 selected from the group consisting of A449, A517, N510, V502, E453, E360, A514, and A460.

13. The protease variant of claim 12, wherein the one or more substitutions at A449, A517, N510, V502, E453, E360, A514, and/or A460 are selected from the group consisting of A449Y, A517T, NS1OH, E360L, E360V, E360C, V502C, E453W, A514T, A514Y, A514D, A514S, and A460W as compared to the Kumamolisin AS as set forth in SEQ ID NO: 1.

* * * * *